(12) United States Patent
Lee et al.

(10) Patent No.: US 10,868,693 B2
(45) Date of Patent: Dec. 15, 2020

(54) HOME DEVICE CONTROL DEVICE AND OPERATION METHOD THEREOF

(71) Applicant: Samsung Electronics Co., Ltd., Suwon-si (KR)

(72) Inventors: Seungjae Lee, Hwaseong-si (KR); Sooyong Kim, Yongin-si (KR); Sangshik Park, Suwon-si (KR); Yongin Park, Seoul (KR); Seoungjae Yoo, Seongnam-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 333 days.

(21) Appl. No.: 15/861,943

(22) Filed: Jan. 4, 2018

(65) Prior Publication Data

US 2018/0359112 A1 Dec. 13, 2018

(30) Foreign Application Priority Data

Jun. 12, 2017 (KR) ........................ 10-2017-0073397

(51) Int. Cl.
```
A61M 21/02       (2006.01)
A61M 21/00       (2006.01)
H04L 12/28       (2006.01)
H04W 4/38        (2018.01)
A61B 5/00        (2006.01)
```
(Continued)

(52) U.S. Cl.
CPC ...... H04L 12/2829 (2013.01); A61B 5/02055 (2013.01); A61B 5/4812 (2013.01); A61B 5/4815 (2013.01); A61M 21/0094 (2013.01); A61M 21/02 (2013.01); H04W 4/38 (2018.02); *A61B 5/0008* (2013.01); *A61B 5/02405* (2013.01); *A61B 5/0531* (2013.01); *A61B 5/0533* (2013.01); *A61B 5/11* (2013.01); *A61B 5/681* (2013.01); *A61B 5/7264* (2013.01);
(Continued)

(58) Field of Classification Search
CPC .............................................. A61M 21/00–02
See application file for complete search history.

(56) References Cited

U.S. PATENT DOCUMENTS

| 7,956,755 B2 | 6/2011 | Lee et al. |
| 8,690,751 B2 | 4/2014 | Auphan |

(Continued)

FOREIGN PATENT DOCUMENTS

| KR | 100923967 B1 | 10/2009 |
| KR | 1020100003757 A | 1/2010 |

OTHER PUBLICATIONS

Masao Yaso et al., "Detection of REM sleep by heart rate", Proceedings of the First International Workshop on Kansei, Feb. 2-3, 2006, Fukuoka, Japan.

*Primary Examiner* — Thaddeus B Cox
(74) *Attorney, Agent, or Firm* — Harness, Dickey and Pierce, P.L.C.

(57) ABSTRACT

An apparatus and a method for controlling a home device using biometric information are provided. The method includes determining a reference sleep pattern among a plurality of sleep patterns based on sleep time information of a user or basic information of the user, analyzing a sleep state of the user based on biometric information of the user, comparing the reference sleep pattern with the sleep state, determining a sleep environmental condition when the reference sleep pattern is different from the sleep state, and controlling the home device based on the determined sleep environmental condition.

11 Claims, 14 Drawing Sheets

(51) Int. Cl.
*A61B 5/0205* (2006.01)
*A61B 5/024* (2006.01)
*H04L 29/08* (2006.01)
*A61B 5/11* (2006.01)

(52) U.S. Cl.
CPC ............... *A61B 2560/0242* (2013.01); *A61B 2562/0204* (2013.01); *A61M 2021/0027* (2013.01); *A61M 2021/0044* (2013.01); *A61M 2205/3375* (2013.01); *A61M 2205/3569* (2013.01); *A61M 2205/3592* (2013.01); *A61M 2205/505* (2013.01); *A61M 2230/06* (2013.01); *A61M 2230/50* (2013.01); *A61M 2230/63* (2013.01); *A61M 2230/65* (2013.01); *H04L 67/12* (2013.01); *H04L 67/125* (2013.01)

(56) References Cited

U.S. PATENT DOCUMENTS

| | | |
|---|---|---|
| 8,768,520 B2 | 7/2014 | Oexman et al. |
| 9,314,583 B2 | 4/2016 | Gavish |
| 9,459,597 B2 | 10/2016 | Kahn et al. |
| 10,252,058 B1* | 4/2019 | Fuerst .................... G16H 10/20 |
| 2010/0048984 A1* | 2/2010 | Anderson ............. A61M 21/02 |
| | | 600/27 |
| 2013/0303837 A1* | 11/2013 | Berka .................. A61M 21/02 |
| | | 600/28 |
| 2016/0213309 A1 | 7/2016 | Sannholm et al. |
| 2016/0338637 A1 | 11/2016 | Shen et al. |
| 2016/0361515 A1 | 12/2016 | Jung et al. |
| 2018/0085549 A1* | 3/2018 | Kaislasaari ............ G16H 40/63 |
| 2018/0177974 A1* | 6/2018 | LaPorte ............... A61B 5/4836 |

* cited by examiner

[Sleep pattern table]

| Conditions | Sleep pattern |
|---|---|
| 6 hours < Sleep time < 7 hours<br>30 < Health condition < 50 | Sleep pattern 1 |
| 1 hour < Sleep time < 2 hours<br>60 < Health condition < 70 | Sleep pattern 2 |
| 3 hours < Sleep time < 4 hours<br>30 < age < 40 | Sleep pattern 3 |

⇒

| Reference sleep pattern |
|---|
| Sleep pattern 2 |

[Sleep time & User basic information]
Sleep time : 1.2 hours
Health condition : 65

HOME DEVICE CONTROL DEVICE AND OPERATION METHOD THEREOF

CROSS-REFERENCE TO RELATED APPLICATIONS

A claim for priority under 35 U.S.C. § 119 is made to Korean Patent Application No. 10-2017-0073397 filed on Jun. 12, 2017, in the Korean Intellectual Property Office, the entire contents of which are hereby incorporated by reference.

BACKGROUND

Example embodiments of the inventive concepts described herein relate to a home device control device and/or a method of controlling a home device. For example, at least some example embodiments relate to, an apparatus and/or method for controlling a home device using biometric information.

With the development of Internet of things (IoT) technologies, there have been many electronic devices which are connected to wired and wireless communication networks and are remotely controlled. Particularly, electronic devices installed in a building may be connected to a wireless communication network and may be remotely controlled for convenience of use and ensuring safety of the building. Electronic devices with which such IoT technologies are combined may be manually controlled by persons and/or may be automatically controlled based on information collected using a variety of sensors.

Home devices with which IoT technologies are combined may constitute a home network system by being connected to a wired and/or wireless network and performing communication. The home devices may be controlled through a home gateway. The home gateway may control the home devices based on data received from one or more user terminals and/or sensors.

A home device may play a role in changing an environment of a home. For example, an air conditioner, a lamp, and the like may be used to create a pleasant sleep environment of a user. If the user sets the operation conditions of home devices such as an air conditioner and a lamp when the user goes to sleep, the home devices may perform their operation without considering a state of the user who takes sleep.

SUMMARY

Example embodiments of the inventive concepts provide a home device control device for enhancing sleep quality of a user and an operation method thereof.

According to an example embodiment, a method of operating a control device for controlling a home device may include determining a reference sleep pattern among a plurality of sleep patterns based on one or more of sleep time information associated with a user and basic information associated with the user; analyzing a current sleep state of the user based on biometric information of the user; comparing the reference sleep pattern with the current sleep state; determining a sleep environmental condition when the reference sleep pattern is different from the current sleep state; and controlling the home device based on the sleep environmental condition.

According to another example embodiment, a control device may include a memory configured to store a plurality of sleep patterns; and a processor configured to, determine a reference sleep pattern among a plurality of sleep patterns based on one or more of sleep time information associated with a user and basic information associated with the user, analyze a current sleep state of a user based on biometric information of the user, compare the reference sleep pattern with the current sleep state, determine a sleep environmental condition when a reference sleep state of the reference sleep pattern is different from the current sleep state of the user, and control a home device based on the sleep environmental condition.

According to another example embodiment, a control device may include a sensor configured to sense biometric information of a user, a memory configured to store a plurality of sleep patterns; and a processor configured to, determine a reference sleep pattern among a plurality of sleep patterns based on one or more of sleep time information associated with the user and basic information associated with the user, analyze a current sleep state of a user based on the biometric information of the user, compare the reference sleep pattern with the current sleep state, determine a sleep environmental condition when a reference sleep state of the reference sleep pattern is different from the current sleep state of the user, and control a home device based on the sleep environmental condition.

According to another example embodiment, a control system may include a wearable device configured to include a sensor configured to sense biometric information of a user, a home device configured to change a sleep environmental condition, a mobile device configured to analyze a sleep state of the user based on the biometric information, compare the sleep state of the user with a reference sleep pattern, and generate a control command for the home device, and a home gateway configured to receive the control command and control the home device. The mobile device may be configured to determine the reference sleep pattern among a plurality of sleep patterns based on sleep time information of the user or basic information of the user.

According to another example embodiment of the inventive concepts, a control device may be configured to control home devices, the control device may include a memory and a processor, the memory including computer readable code that, when executed by the processor, configures the processor to, analyze a current sleep state of a user based on biometric information associated with the user, and selectively control one or more of the home devices based on the current sleep state of the user.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
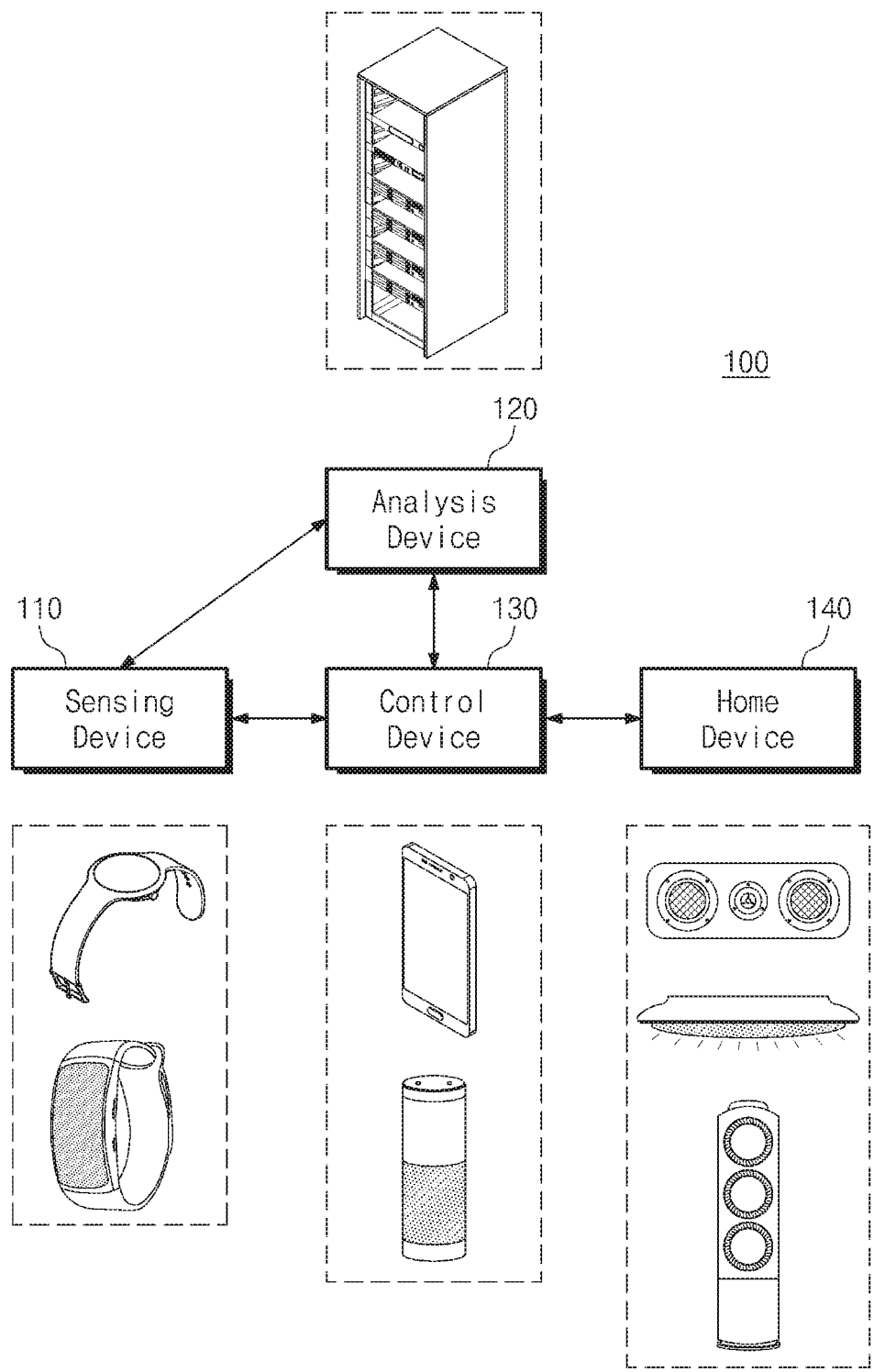
FIG. 1 is a block diagram illustrating a configuration of a home device control system according to an example embodiment of the inventive concepts.

Hereinafter, example embodiments of the inventive concepts are described with reference to the accompanying drawings so that this disclosure will be thorough and complete and will fully convey the scope of example embodiments of the inventive concepts to those skilled in the art, FIG. 1 is a block diagram illustrating a configuration of a home device control system according to an example embodiment of the inventive concepts.

Referring to FIG. 1, a home device control system 100 may include a sensing device 110, an analysis device 120, a control device 130; and a home device 140. The sensing device 110, the analysis device 120, the control device 130, and the home device 140 may be connected with each other by a wired or wireless communication network.

The sensing device 100 may include at least one of a temperature sensor, a heart rate sensor, an acceleration sensor, a sound sensor, and a galvanic skin response (GSR) sensor. The sensors included in the sensing device 110 may sense biometric information of a user who wears the sensing device 110. The biometric information may include all of information which may be measured from a body of the user by the sensing device 110. For example, the biometric information may include a skin temperature, heart rate variability (HRV), movement of the body, a sound generated from the user, and a GSR.

The sensing device 110 may obtain basic information of the user, including a gender, an age, a health condition, and body information, or combinations thereof of the user, and sleep time information including an alarm time and the like via its input interface. For example, the input interface may include a keypad, a touch pad, a button-type switch, a dial switch, a microphone, and the like.

The sensing device 110 may transmit the biometric information of the user, sensed by the sensor, to the analysis device 120 and the control device 130. The sensing device 110 may transmit the basic information of the user, the sleep time information, and the like, obtained via the input interface, to the analysis device 120 and the control device 130.

The sensing device 110 may include a wearable device which may be worn or attached to a body of the user. For example, the sensing device 110 may be a band or a watch worn on a wrist of the user. The sensing device 110 is not limited to a device, such as the band or the watch, which covers a body of the user, and may include all devices which may be worn or attached to the body of the user.

The analysis device 120 may receive biometric information of the user from the sensing device 110 or the control device 130. The analysis device 120 may analyze a sleep state of the user from his or her biometric information. For example, the analysis device 120 may classify the sleep state of the user as a wake state, a light sleep state, or a deep sleep state. Further, the analysis device 120 may classify the sleep state of the user as a rapid eye movement (REM) sleep state or a non REM (NREM) sleep state. The NREM sleep state may be classified as a first stage NREM1, a second stage NREM2, a third stage NREM3, or a fourth stage NREM4. As an NREM sleep stage is more increased, it may be determined that the user is in a deeper sleep state.

The REM sleep state may be a time when oxygen consumption of a brain and cerebral blood flow are increased and when the brain is functionally activated. In the REM sleep state, fast movement of eyes, irregular breathing, and an irregular heart rate may be detected together with an alpha wave of 8 to 13 Hz. The NREM sleep state may be a time when body tissue is repaired, when parasympathetic is activated, and when a body temperature is adjusted to be low. Further, in the NREM sleep state, a heart rate, a cardiac output, and blood pressure may be reduced. As described above, the NREM sleep state may be divided into the four stages. In the first stage NREM1, a theta wave of 4 to 7 Hz and slow eye movement may appear. In the second stage NREM2, a sleep spindle of 12 to 14 Hz may appear. In the third and fourth stages NREM3 and NREM4, a delta wave may appear. When the delta wave is 20 to 50%, the NREM sleep state may be classified as the third stage NREM3. When the delta wave is greater than or equal to 50%, the NREM sleep state may be classified as the fourth stage NREM4. Each of the first and second stages NREM1 and NREM2 of the NREM sleep state may correspond to a light sleep state, and each of the third and fourth stages NREM3 and NREM4 of the NREM sleep state may correspond to a deep sleep state.

As such, since a sleep feature varies according to each sleep state, the analysis device 120 may analyze a sleep state of the user from his or her biometric information.

The analysis device 120 may generate a sleep pattern based on feedback information on a sleep state of the user and quality of his or her sleep. For example, the analysis device 120 may generate a sleep pattern by analyzing a sleep state at a desired (or, alternatively, a predetermined) interval of time during a total sleep time of the user. The analysis device 120 may extract a sleep pattern of the user from a plurality of analyzed sleep state information. In other words, the sleep pattern may be information indicating a change in sleep state according to a sleep time.

The analysis device 120 may determine a reference sleep pattern, which is a criterion for the user to take a deep sleep, among the generated sleep patterns. In other words, the reference sleep pattern may be a sleep pattern including sleep state information, which is a criterion for the user to take a deep sleep, among sleep patterns.

The analysis device 120 may generate a sleep pattern based on feedback information on quality of sleep of the user. Sleep feedback information including a value of sleep quality during a sleep time may be obtained via an input interface of the sensing device 110 from the user. Further, the sleep feedback information of the user may be calculated from his or her biometric information by the analysis device 120. If the value of sleep quality is greater than a threshold, the analysis device 120 may generate a sleep pattern using sleep state information analyzed from the sleep. A threshold for sleep quality may be a reference value for determining the sleep quality. The threshold for the sleep quality may be a value previously stored in the analysis device 120. The user may verify the threshold for the sleep quality and may input his or her sleep feedback information on the basis of the threshold.

For example, if the value of the sleep quality is 90 and if the threshold is 88, the analysis device 120 may determine that the sleep quality of the user is good and may generate a sleep pattern using sleep state information analyzed over time. The analysis device 120 may store a sleep pattern generated to determine a reference sleep pattern. For example, the value of the sleep quality may include satisfaction with sleep of the user or a stress level calculated from his or her biometric information during sleep. For example, if a maximum value of sleep quality is 100, the analysis device 120 may obtain satisfaction with sleep among values greater than the threshold and less than or equal to 100 from the user. Further, the analysis device 120 may calculate a stress level among the values greater than the threshold and less than or equal to 100 from biometric information of the user during sleep.

The analysis device 120 may determine one of a plurality of stored sleep patterns as a reference sleep pattern. The analysis device 120 may determine a reference sleep pattern based on the basic information of the user or the sleep time information. For example, the analysis device 120 may determine a sleep pattern on the basis of a total sleep time, a gender, an age, and a health condition, and the like of the user. The analysis device 120 may calculate an expected sleep time of the user from sleep time information and may determine a sleep pattern corresponding to the sleep time as a reference sleep pattern. The analysis device 120 may transmit data for the analyzed sleep state of the user and the reference sleep pattern to the control device 130.

The analysis device 120 may be included in an external server such as a cloud server. Further, the analysis device 120 may be included in an electronic device which exists in a space where the user takes sleep.

The control device 130 may control an operation of the home device 140 based on collected information. For example, the control device 130 may control the home device 140 from a reference sleep pattern received from the analysis device 120 and a sleep state of the user. The control device 130 may compare the reference sleep pattern with a current sleep state of the user. If a sleep state of the reference sleep pattern is not equal to the current sleep state of the user, the control device 130 may control an operation of the home device 140. The control device 130 may transmit a control signal to the home device 140 for changing a sleep environmental condition such that the current sleep state is identical to the sleep state of the reference sleep pattern. For example, the control device 130 may transmit a control signal for changing a temperature of a room to an air conditioner to control an operation of the air conditioner.

The control device 130 may be included in a home gateway for controlling the home device 140 or a user terminal such as a smartphone. If the analysis device 120 is included in the external server such as the cloud server, the control device 130 may include a communication module for performing wireless communication with the analysis device 120. The control device 130 may access a wired and wireless network, such as the Internet, and may transmit and receive data with the analysis device 120.

Similar to the sensing device 110, the control device 130 may obtain sleep feedback information of the user via the input interface from the user. Further, the control device 130 may obtain the basic information of the user and the sleep time information via the input interface and may transmit the obtained information to the analysis device 120.

The home device 140 may operate in response to a control signal of the control device 130. For example, if the control device 130 transmits a control signal to the at least one home device 140, the at least one home device 140 which receives the control signal may operate according to the control signal.

The home device 140 may transmit and receive data according to a wired or wireless communication mode. For example, the home device 140 may receive a control command from the control device 130 and may transmit state information about the home device 140 and detected sleep environment information to the control device 130. The control device 130 may control an operation of the home device 140 based on the state information and the sleep environment information received from the home device 140. For example, if receiving fault state information from the home device 140, the control device 130 may control another home device except for the faulty home device 140 in changing a sleep environmental condition. Further, the control device 130 may control an operation of an air conditioner based on temperature information detected from the air conditioner.

The home device control system 100 according to example embodiments of the inventive concepts is not limited thereto, and may include various types of home device control systems for performing the same function.

Figure 2:
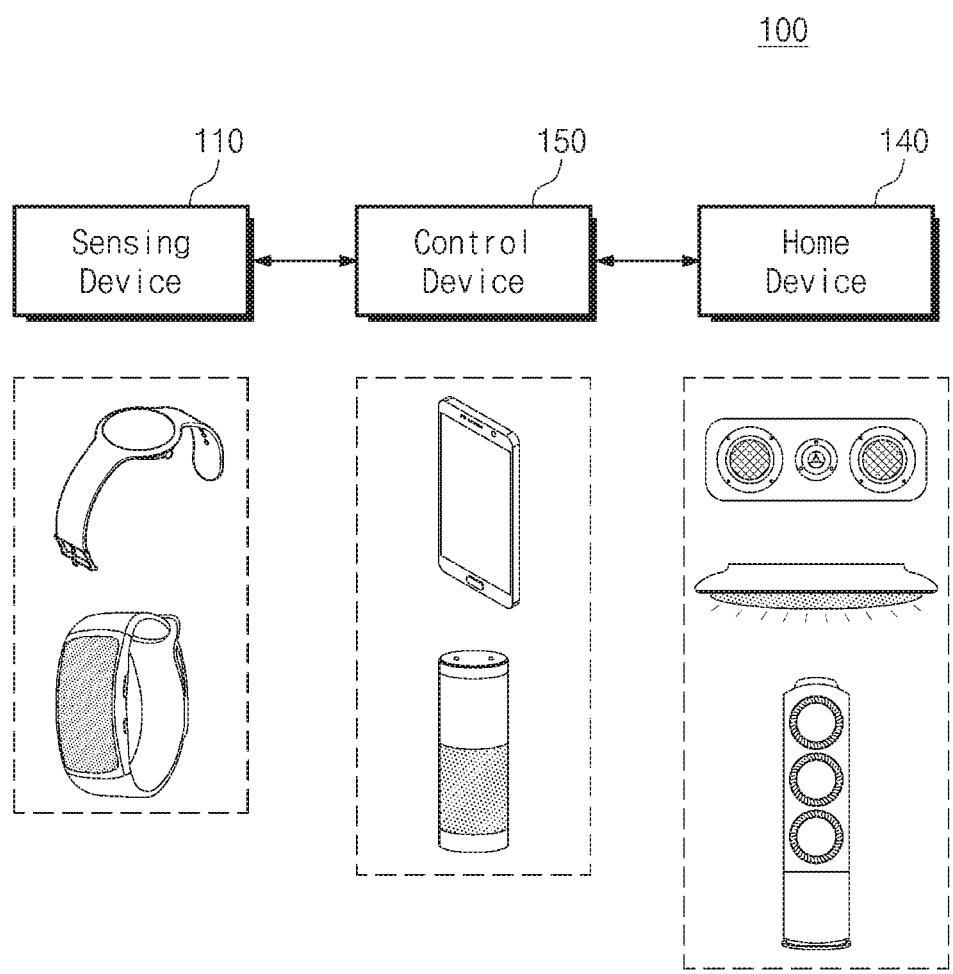
FIG. 2 is a block diagram illustrating a configuration of a home device control system according to another example embodiment of the inventive concepts.

FIG. 2 is a block diagram illustrating a configuration of a home device control system according to another example embodiment of the inventive concepts.

Referring to FIG. 2, a home device control system 100 may include a sensing device 110, a home device 140, and a control device 150. Since the sensing device 110 and the home device 150 of FIG. 2 are the same as a sensing device 110 and a home device 140 described in a home device control system 100 of FIG. 1, a description will be omitted.

The control device 150 may generate a sleep pattern by receiving biometric information of a user and analyzing his or her sleep state. Further, the control device 150 may control the home device 140 based on a result of comparing a current sleep state with a reference sleep pattern. In other words, the control device 150 may include all of functions of an analysis device 120 and a control device 130 of FIG. 1. Since the control device 150 performs the same function as the analysis device 120 and the control device 130 of FIG. 1, a repeated description will be omitted.

If a home device control system is configured without the separate analysis device 120 like the home device control system 100 of FIG. 2, the sensing device 110 and the control device 150 may not perform communication with the analysis device 120. For example, the control device 150 may be a user terminal or a home gateway, which communicates with the home device 140.

Figure 3:
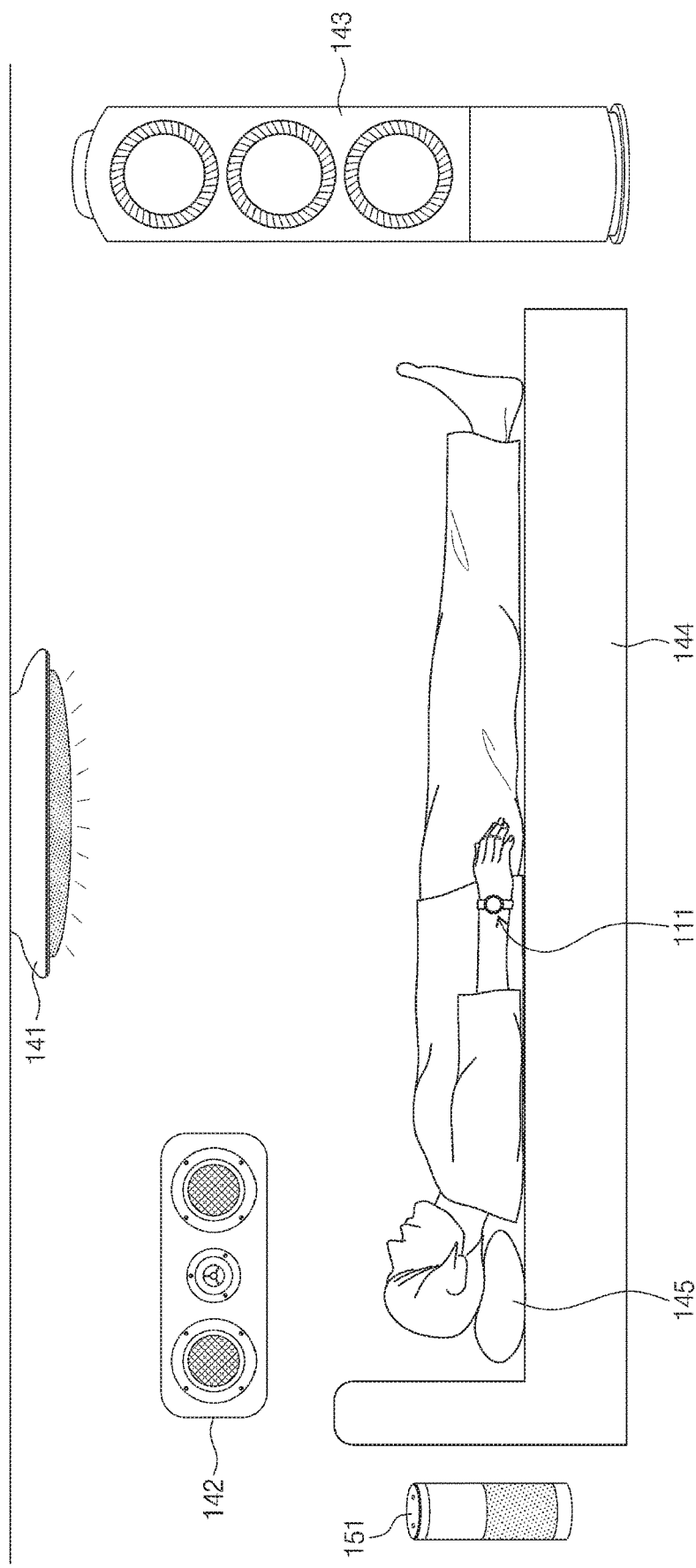
FIG. 3 is a drawing illustrating an example of a home device control system of FIG. 2.

FIG. 3 is a drawing illustrating an example of a home device control system of FIG. 2.

Referring to FIGS. 2 and 3, a wearable device 111 worn on a wrist of a user may correspond to a sensing device 110. For example, a temperature sensor, a heart rate sensor, an acceleration sensor, a sound sensor, a GSR sensor, and the like may be mounted on the wearable device 111. As worn in a state it is in contact with a body of the user, the wearable device 111 may detect a skin temperature from the temperature sensor and may detect HRV (Heart Rate Variability) from the heart rate sensor. The wearable device 111 may detect movement of the user from the acceleration sensor and may detect snoring and sleep talking of the user from the sound sensor. Further, the wearable device 111 may detect a GSR from the GSR sensor.

A home gateway 151 may analyze a sleep state, sleep quality, and the like based on biometric information detected by the wearable device 111. For example, the home gateway 151 may calculate a skin impedance value from the GSR of the user and may calculate a value of sleep quality corresponding to the skin impedance value. If the skin impedance value of the user is low, the home gateway 151 may calculate a value of sleep quality of the user as a high value. In other words, if the skin impedance value of the user is low, the home gateway 151 may determine that the sleep quality of the user is good.

The home gateway 151 may include a function of a control device 150 of FIG. 2. The home gateway 151 may generate a sleep pattern and analyzing a sleep state by receiving biometric information detected by the wearable device 111 from the wearable device 111. The home gateway 151 may determine at least one of the sleep patterns as a reference sleep pattern. The home gateway 151 may compare a current sleep state with the reference sleep pattern to control home devices 141 to 145. The home gateway 151 may control the home devices 141 to 145 to change a sleep environmental condition of the user.

For example, the home gateway 151 may control a lamp 141 to adjust brightness, a color, and a direction of light and may control the speaker 142 to adjust a level of a sound and whether to play back music. The home gateway 151 may control an air conditioner 143 to adjust temperature and a direction and strength of a wind and may control a bed 144 to adjust an incline and a shake of the bed 144. Further, the home gateway 151 may control a pillow 145 to adjust a height and a temperature of the pillow 145.

After sleep of the user is completed, the home gateway 151 may transmit sleep feedback information, including sleep quality, a sleep state, and a reference sleep pattern of the user during a sleep time and operation information of the home devices 141 to 145, to the wearable device 111. The user may verify feedback information on his or her sleep through the wearable device 111 or the home gateway 151.

Each of the home devices 141 to 145 may include a communication module to be wirelessly connected with the home gateway 151. Further, each of the home devices 141 to 145 may be a smart device which performs various operations according to a control command of the home gateway 151. A home device 140 which may change a sleep environmental condition of the user is not limited to the devices 141 to 145 shown in FIG. 3, and may include all smart devices which may change the sleep environmental condition of the user.

Further, in some example embodiments of the inventive concepts, while FIG. 2 illustrates a sensing device 110 and a control device 150 may be implemented as separate devices, in some example embodiments, the sensing device 110 and the control device 150 may be implemented to be included in one electronic device (not shown). If the sensing device 110 and the control device 150 are included in the one electronic device, the home device 140 may be controlled for a deep sleep using only the electronic device. For example, all of functions of the sensing device 110 and the control device 150 are included in one wearable device worn or attached to a body of the user, the home device 140 may be controlled for a deep sleep using only the one wearable device.

Hereinafter, a description will be given in detail of a method for controlling a home device according to an example embodiment of the inventive concepts with reference to FIG. 4. For concise description, a description will be given of the method for controlling the home device according to an example embodiment of the inventive concepts with reference to a control device 150 of FIG. 2. However, the scope of the example embodiments of the inventive concepts are not limited thereto. For example, the method for controlling the home device according to an example embodiment of the inventive concepts may be performed through various types of electronic devices, each of which includes a function of the control device 150. For example, the method for controlling the home device may be performed by one wearable device including both of functions of a sensing device 110 and a control device 150. Further, the function of the control device 150 may be performed by a mobile device of the user and a home gateway.

Figure 4:
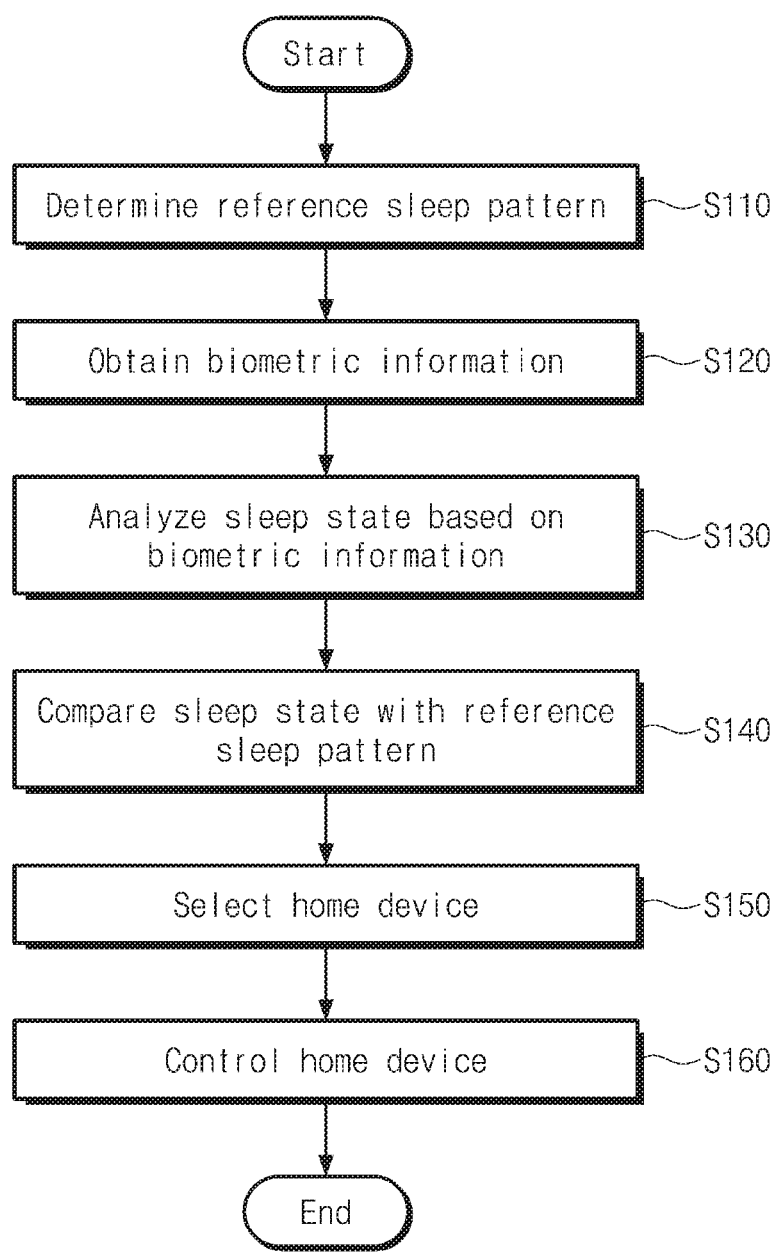
FIG. 4 is a flowchart illustrating a method for controlling a home device according to an example embodiment of the inventive concepts.

FIG. 4 is a flowchart illustrating a method for controlling a home device according to an example embodiment of the inventive concepts.

Referring to FIGS. 2 and 4, in operation S110, the control device 150 may determine a reference sleep pattern by determining sleep time information, basic information of a user, and the like.

For example, the control device 150 may determine the sleep time information of the user from his or her alarm setting time to determine the reference sleep pattern. The control device 150 may calculate a total sleep time of the user by collecting his or her alarm setting time information and may determine the reference sleep pattern based on the total sleep time. The control device 150 may determine the reference sleep pattern that is suitable for the user in consideration of the sleep time information and the basic information of the user among a plurality of sleep patterns previously stored in the control device 150. Thus, the control device 150 may adjust a sleep environmental condition during a sleep time on the basis of the determined reference sleep pattern. The sleep patterns previously stored in the control device 150 may include a sleep pattern generated by the control device 150, a sleep pattern received from an external server, and/or a sleep pattern stored in advance in the control device 150.

A description will be given in detail of the method for determining the reference sleep pattern in operation S110 of FIG. 4 later with reference to FIGS. 5 to 8, discussed below.

In operation S120, the control device 150 may obtain biometric information from a sensing device 110. A description will be given in detail of the method for obtaining the biometric information of the user in operation S120 of FIG. 4 later with reference to FIG. 9, discussed below.

In operation S130, the control device 150 may analyze a sleep state of the user based on the obtained biometric information. The control device 150 may analyze a sleep state of the user using at least one of a plurality of biometric information. For example, the control device 150 may analyze the sleep state of the user using at least one of a skin temperature, HRV, movement of the user, a sound generated from him or her, and a GSR.

The control device 150 may analyze a sleep state of the user among a wake state, a REM sleep state, and an NREM sleep state (first to fourth stages NREM1 to NREM4). The control device 150 may classify each of the first and second stages NREM1 and NREM2 in the NREM sleep state as a light sleep state, and may classify each of the third and fourth stages NREM3 and NREM4 in the NREM state as a deep sleep state.

A description will be given in detail of a method for analyzing a sleep state in operation S130 of FIG. 4 later with reference to FIG. 10, discussed below.

In operation S140, the control device 150 may compare a current sleep state of the user with the reference sleep pattern. The reference sleep pattern may include information about a specific sleep state changed over time. The control device 150 may compare a sleep state of a time corresponding to a current time among sleep states included in the reference sleep pattern with an analyzed current sleep state. If the sleep state of the reference sleep pattern is identical to the current sleep state, the control device 150 may not transmit a separate control command to one or more of the home devices 140. If the sleep state of the reference sleep pattern is different from the current sleep state, the control device 150 may perform an operation for changing a sleep environmental condition.

In operation S150, the control device 150 may select one or more of the home devices 140 to which a control command will be transmitted to change a sleep environmental condition. For example, the control device 150 may determine at least one of a plurality of sleep environmental conditions and may select one or more of the home devices 140 based on the determined sleep environmental condition.

Further, the control device 150 may select one or more of the home devices 140 based on state information of the home devices 140 or setting information of the user. For example, the control device 150 may exclude a device which is in a fault state among devices included in the home devices 140 from an object to be selected. The control device 150 may collect information about a preferred or non-preferred device of the user and may primarily select the preferred one of the home devices 140.

In operation S160, the control device 150 may transmit a control command to the selected ones of the home devices 140 to control the selected ones of the home devices 140.

A description will be given in detail of an operation of the control device 150 in operations S140 to S160 of FIG. 4 later with reference to FIGS. 11 and 12.

Hereinafter, a description will be given in detail of the method for determining the reference sleep pattern in operation S110 of FIG. 4 with reference to FIGS. 5 to 8.

Figure 5:
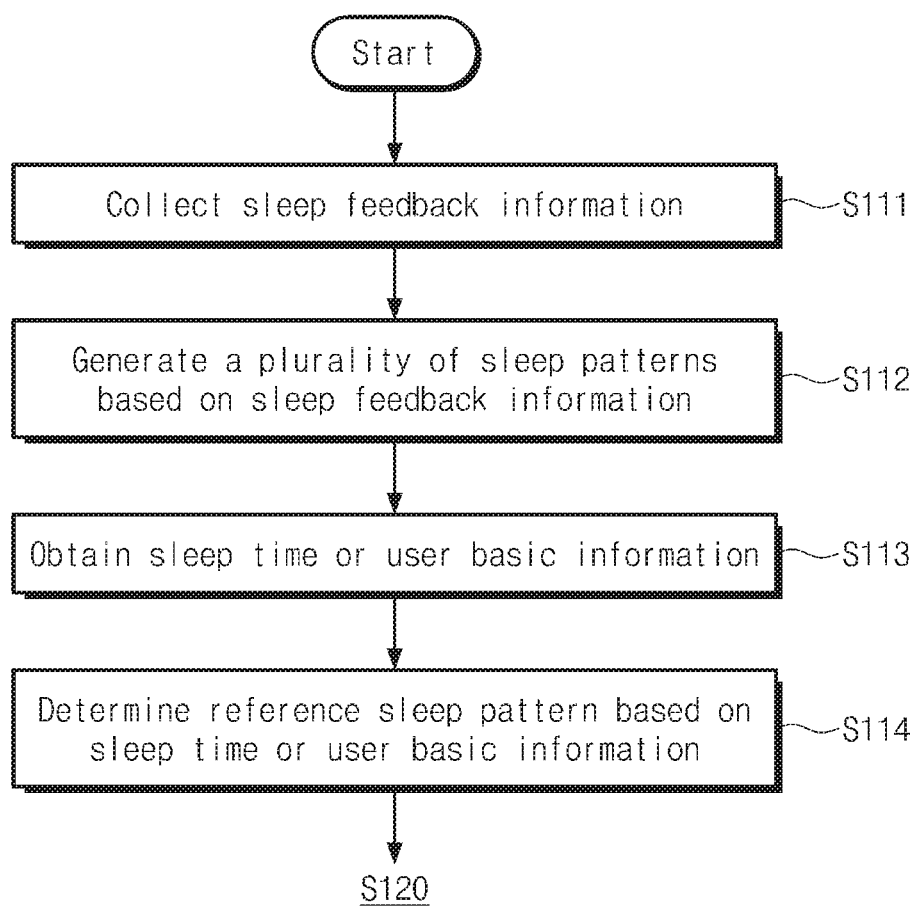
FIG. 5 is a flowchart illustrating a method for determining a reference sleep pattern according to an example embodiment of the inventive concepts.
Figure 6:
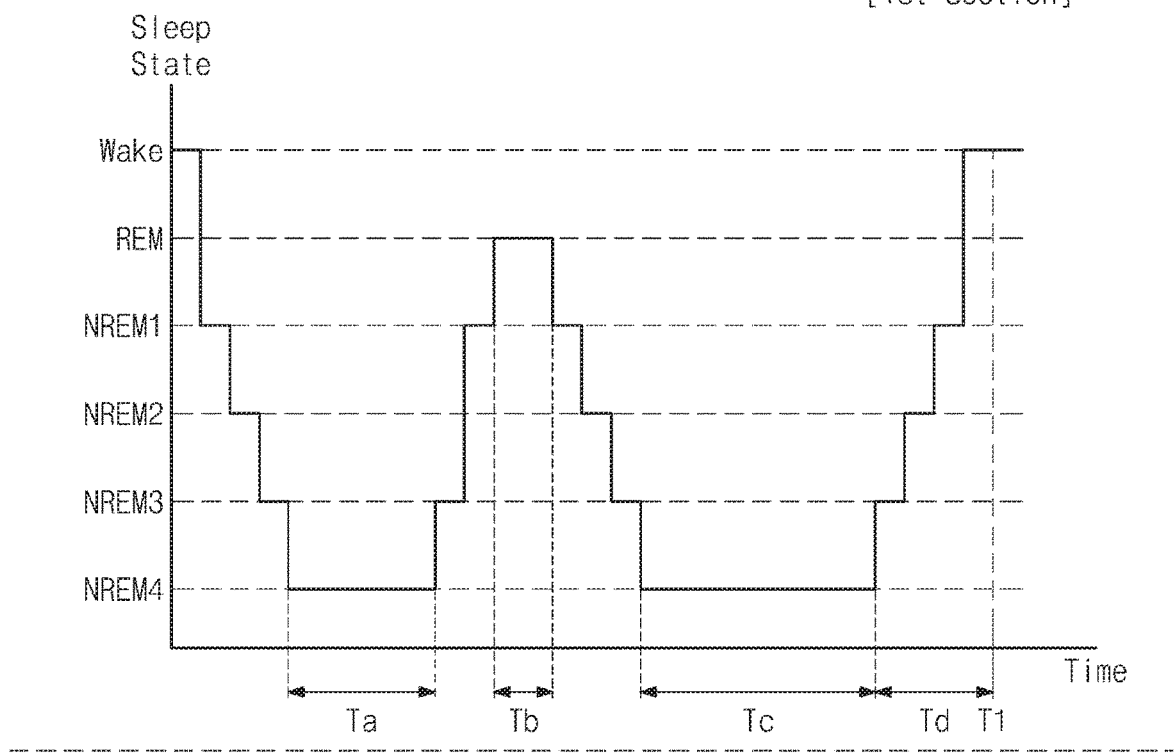
FIG. 6 is a waveform chart illustrating an example of a sleep pattern according to an example embodiment of the inventive concepts.
Figure 6:
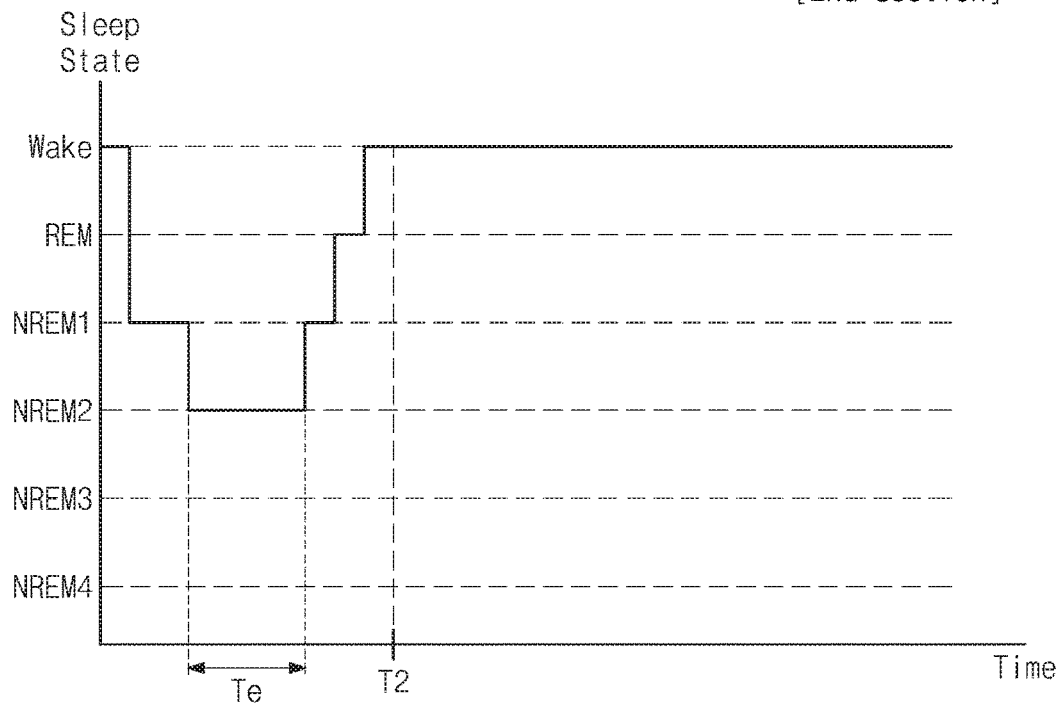
Figure 7:
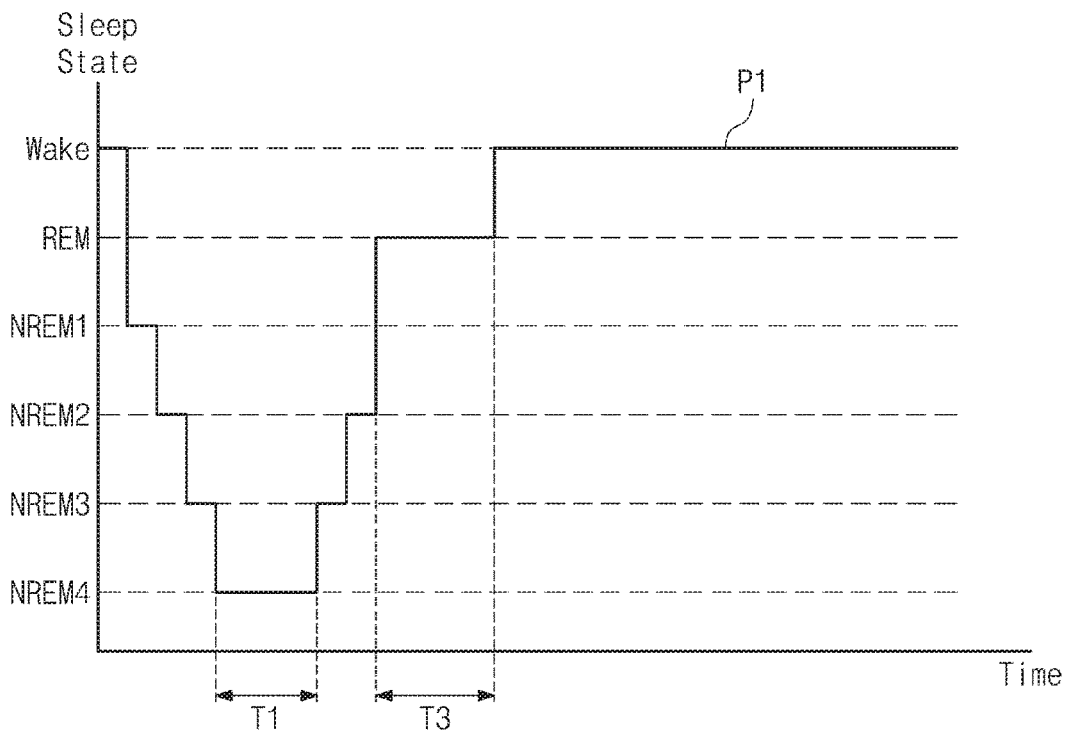
FIG. 7 is a waveform chart illustrating an example of generating a sleep pattern according to an example embodiment of the inventive concepts.
Figure 7:
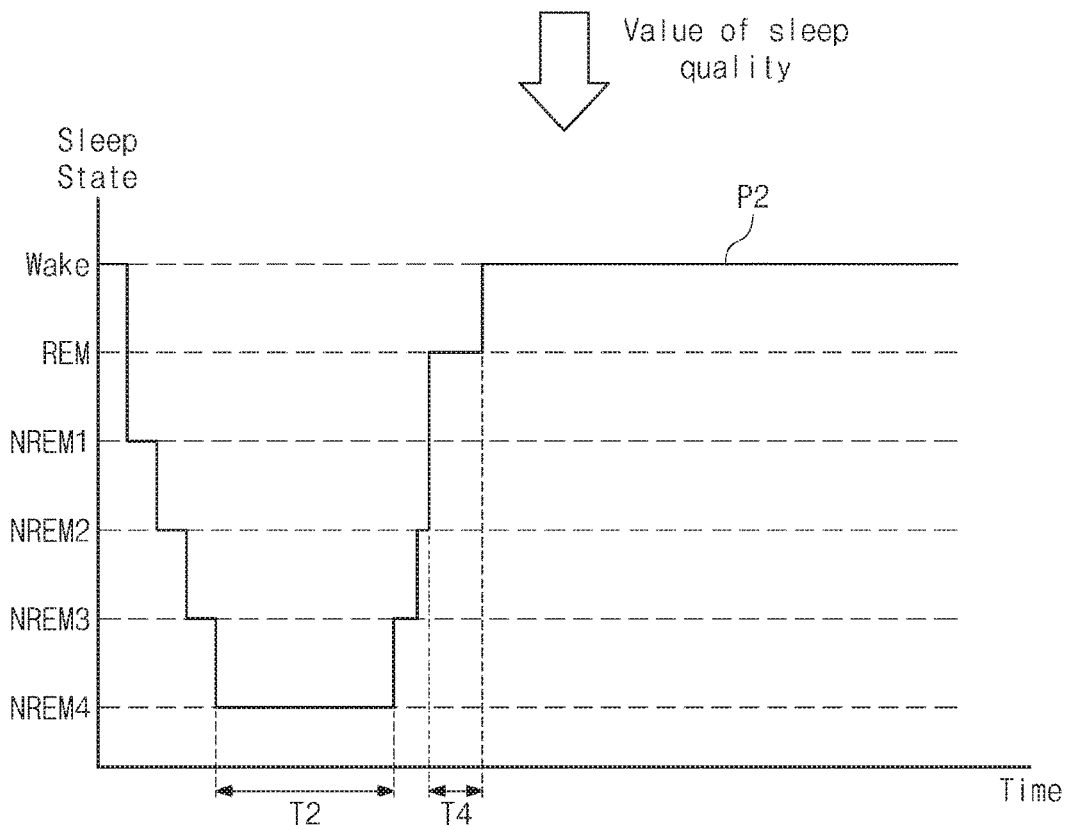
Figures 8, 9:
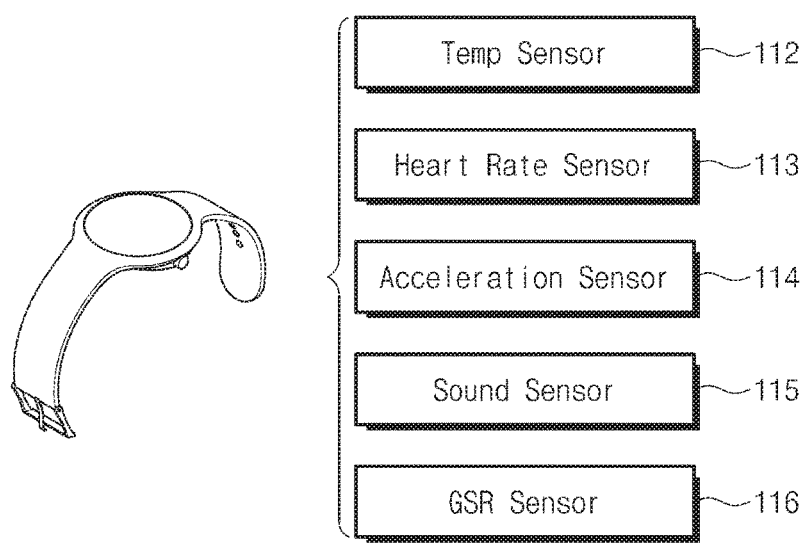
FIG. 8 is a table illustrating an example of determining a reference sleep pattern according to an example embodiment of the inventive concepts.
FIG. 9 is a block diagram illustrating an example of a sensing device of FIG. 2.

FIG. 5 is a flowchart illustrating a method for determining a reference sleep pattern according to an example embodiment of the inventive concepts. FIG. 6 is a waveform chart illustrating an example of a sleep pattern according to an example embodiment of the inventive concepts. FIG. 7 is a waveform chart illustrating an example of generating a sleep pattern according to an example embodiment of the inventive concepts. FIG. 8 is a table illustrating an example of determining a reference sleep pattern according to an example embodiment of the inventive concept.

Referring to FIG. 2 and FIGS. 5 to 8, in operation S111, the control device 150 may collect sleep feedback information. The sleep feedback information may include a value of sleep quality, received from a user after his or her sleep is completed or a value of sleep quality, analyzed in the control device 150.

For example, in some example embodiments, the user may input a value of sleep quality via an input interface of a sensing device 110 or the control device 150 after his or her sleep. In other example embodiments, the control device 150 may calculate a value of sleep quality of the user from obtained biometric information. For example, the control device 150 may calculate a skin impedance value from a GSR of the user, measured by a GSR sensor, and may calculate a value of sleep quality according to the skin impedance value. If the skin impedance value is low, the control device 150 may calculate a value of sleep quality to be low. If the skin impedance value is high, the control device 150 may calculate a value of sleep quality to be high.

The control device 150 may calculate a value of sleep quality continuously during a total sleep time of the user. For example, the control device 150 may calculate a value of sleep quality with respect to a specific time in the total sleep time of the user to be low and may calculate a value of sleep quality with respect to a specific time in the total sleep time to be high. Thus, there may be an interval where a value of sleep quality is low in the total sleep time of the user and an interval where a value of sleep quality is high in the total sleep time.

In operation S112, the control device 150 may generate a sleep pattern based on the sleep feedback information. The sleep pattern may be information in which a sleep state changed during a sleep time of the user is calculated over a sleep time. The sleep pattern may vary according to basic information of the user, including a gender, an age, a health condition, and a body characteristic of the user, and sleep time information. The control device 150 may extract a value of sleep quality from the sleep feedback information and may generate a sleep pattern using sleep state information in corresponding sleep if the value of the sleep quality is high. Further, the control device 150 may generate a sleep pattern using sleep state information in an interval where a value of sleep quality is high during a sleep time of the user.

The control device 150 may previously store sleep patterns generated in various situations. For example, as shown in FIG. 6, a plurality of sleep patterns may be previously stored in the control device 150. A $1^{st}$ section of FIG. 6 may indicate a sleep pattern when a total sleep time of the user is a first time T1, and a $2^{nd}$ section may indicate a sleep pattern when the total sleep time is a second time T2. The sleep pattern of the $1^{st}$ section may be a sleep pattern when a sleep time is long, and the sleep pattern of the $2^{nd}$ section may be a sleep pattern when a sleep time is short. For example, if an expected sleep time of the user is longer than a first threshold, the control device 150 may determine the sleep pattern of the $1^{st}$ section as a reference sleep pattern. Further, if the expected sleep time is shorter than a second threshold, the control device 150 may determine the sleep pattern of the $2^{nd}$ section as the reference sleep pattern.

The first threshold and the second threshold for determining the reference sleep pattern may be values generated in the control device 150 on the basis of a total sleep time of a stored sleep pattern. For example, if the total sleep time of the stored sleep pattern is the first time T1, the control device 150 may generate a value, which is less than the first time T1, as the first threshold. If the total sleep time of the stored sleep pattern is the second time T2, the control device 150 may generate a value, which is greater than the second time T2, as the second threshold. In other words, each of the first threshold and the second threshold may be a threshold time which is a criterion for determining a reference sleep pattern among a plurality of stored sleep patterns. The method for generating a threshold for determining the reference sleep pattern in the present disclosure is not limited to the above-mentioned details. A threshold may be generated in various methods.

A horizontal axis of a sleep pattern may indicate time, and a vertical axis may indicate a sleep state. The sleep state may be classified as a wake state, a REM sleep state REM, a first stage NREM1 of an NREM sleep state, a second stage NREM2 of the NREM sleep state, a third stage NREM3 of the NREM sleep state, or a fourth stage NREM4 of the NREM sleep state.

Referring to the sleep pattern of the $1^{st}$ section, the fourth stage NREM4 of the NREM sleep state may be indicated in two intervals Ta and Tc during a total sleep time and the REM sleep state REM may be indicated in one interval Tb. Further, a stage of the NREM sleep state may be sequentially reduced in the closest interval Td to the time T when sleep is completed. If the user immediately awakes from a deep sleep state, sleep quality of the user may be bad. Thus, a sleep pattern may be generated such that a stage of the NREM sleep state is reduced at a time when sleep of the user is completed, such that the user wakes from a light sleep state.

Referring to the sleep pattern of the $2^{nd}$ section, the second stage NREM2 of the NREM sleep state may be indicated in one interval Te during a total sleep time. If a sleep time is short and if the user falls into deep sleep NREM3 or NREM4, sleep quality may be bad. Thus, a sleep pattern may be generated not to include the third and fourth stages NREM3 and NREM4 of the NREM sleep state.

While FIG. 6 illustrates an example of various sleep patterns, a sleep pattern according to example embodiments of the inventive concepts are not limited thereto. As described above, there may be a variety of sleep patterns according to a gender, an age, a body characteristic, a sleep time, and a health condition of the user.

The control device 150 may newly generate a previously stored sleep pattern based on sleep feedback information of the user. For example, the control device 150 may correct a previously stored sleep pattern from sleep feedback information of the user. For example, as shown in FIG. 7, the control device 150 may correct a first sleep pattern P1 as a second sleep pattern P2 based on sleep feedback information including a value of sleep quality. In the first sleep pattern P1, the fourth stage NREM4 of the NREM sleep stage may be maintained by time T1 and the REM sleep state REM may be maintained by time T3. First of all, the control device 150 may control a sleep environment of the user based on the first sleep pattern P1. After sleep of the user is completed, if a value of his or her sleep quality is less than or equal to a threshold in the fourth stage of the NREM sleep state NREM4 and the REM sleep state, the control device 150 may adjust a time of the fourth stage of the NREM sleep state NREM4 and a time of the REM sleep state. The control device 150 may generate the new second sleep pattern P2 by increasing the time of the fourth stage of the NREM sleep state NREM4 to time T2 and decreasing the time of REM sleep state to time T4. The control device 150 may store the newly generated second sleep pattern P2 and may delete the previously stored first sleep pattern P1.

The control device 150 may generate various sleep patterns according to various sleep situations of the user. The control device 150 may generate a desired alternatively, an optimum) sleep pattern suitable for the user using collected sleep feedback information. For example, the control device 150 may generate the desired (or, alternatively, the optimum) sleep pattern by comparing sleep patterns in the same situation through machine learning.

In operation S113, the control device 150 may obtain sleep time information and/or basic information of a user. The sleep time information may include information about a total sleep time calculated from an alarm time. The basic information of the user may include a gender, an age, and a health condition of the user and anything unusual of his or her body.

In operation S114, the control device 150 may determine a reference sleep pattern based on the sleep time information and/or the basic information of the user. For example, the control device 150 may determine the reference sleep pattern based on at least one of the sleep time information and the basic information of the user. The control device 150 may match and store a sleep pattern corresponding to a specific condition with the specific condition. For example, the control device 150 may match and store the sleep time information of the user and/or the basic information of the user with a sleep pattern corresponding to the information. The control device 150 may determine a sleep pattern suitable for the user among a plurality of stored sleep patterns as a reference sleep pattern based on the sleep time information of the user and/or the basic information of the user.

For example, a sleep pattern table of FIG. 8 shows a sleep pattern matched with a condition for a specific situation. If a sleep time is between 6 hours and 7 hours and if a health condition value of the user is between 30 and 50, sleep pattern 1 may be matched. If the sleep time is between 1 hour and 2 hours and if the health condition value of the user is between 60 and 70, sleep pattern 2 may be matched. If the sleep time is between 3 hours and 4 hours and if an age of the user is between 30 and 40, sleep pattern 3 may be matched.

For example, as illustrated in FIG. 8, if a sleep time of the user who starts sleep is 1. 2 hours and if the health state value of the user is 65, the control device 150 which stores such a sleep pattern table may determine sleep pattern 2 as a reference sleep pattern. The health condition value of the user may be a value input after the user converts his or her health condition into a numeric value before he or she starts sleep. After the user ends sleep, a sleep time and a health condition value of the user may be matched with an analyzed sleep pattern according to a value of sleep quality and may be stored in the sleep pattern table.

In other words, the control device 150 may store a plurality of sleep patterns respectively matched with various situations of the user and may determine a sleep pattern suitable for the user among a plurality of stored sleep patterns as a reference sleep pattern based on a sleep time of the user who starts sleep and/or the basic information the user.

Hereinafter, a description will be given in detail of the method for obtaining the biometric information of the user in operation S120 of FIG. 4 with reference to FIG. 9.

FIG. 9 is a block diagram illustrating an example of a sensing device of FIG. 2.

Referring to FIGS. 2 and 9, a sensing device 110 may include a temperature sensor 112, a heart rate sensor 113, an acceleration sensor 114, a sound sensor 115, and/or a GSR sensor 116. As shown in FIG. 9, the sensing device 110 may include a band-type wearable device which may be worn on a body of a user.

The sensing device 110 may measure a skin temperature of the user using the temperature sensor 112 and may transmit the temperature information to a control device 150. The sensing device 110 may measure heart rate information using the heart rate sensor 113 and may transmit the measured heart rate information to the control device 150. The sensing device 110 may measure movement information of the user using the acceleration sensor 114 and may transmit the measured movement information to the control device 150. The sensing device 110 may measure sound information generated from the user using the sound sensor 115 and may transmit the measured sound information to the control device 150. For example, the sound sensor 115 may sense snoring, sleep talking, and the like of the user and may transmit the measured sound information to the control device 150. The sensing device 110 may measure skin impedance information through a GSR of the user using the GSR sensor 116 and may transmit the measured skin impedance information to the control device 150.

In other words, the biometric information of the user may include a skin temperature detected from the user, HRV, movement of the user, a sound generated from the user, skin impedance, or combinations thereof.

The control device 150 may obtain biometric information of the user from the sensing device 110.

Hereinafter, a description will be given in detail of a method for analyzing a sleep state in operation S130 of FIG. 4.

Figure 10:
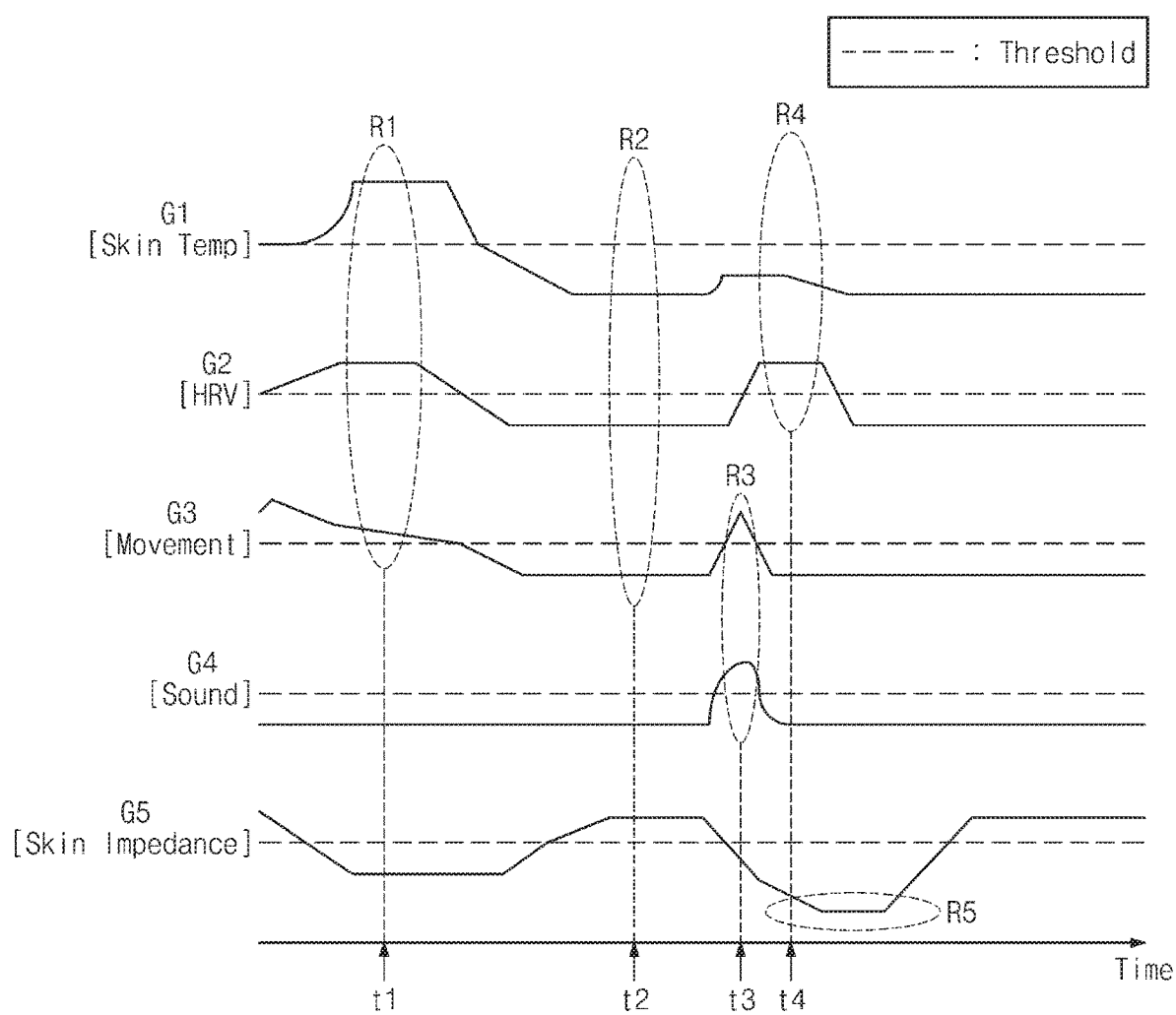
FIG. 10 is a waveform chart illustrating an example of analyzing a sleep state from biometric information according to an example embodiment of the inventive concepts.

FIG. 10 is a waveform chart illustrating an example of analyzing a sleep state from biometric information according to an embodiment of the inventive concept. FIG. 10 includes a graph showing a change in biometric information over time. First graph G1 indicates a change in a skin temperature of a user. Second graph G2 indicates a change in an HRV level of the user. Third graph G3 indicates a change in a movement size of the user. Fourth graph G4 indicates a change in a sound level generated from the user. Fifth graph G5 indicates a change in a skin impedance level through a GSR of the user.

Referring to FIGS. 2 and 10, the control device 150 may analyze a sleep state of the user using at least one of a plurality of biometric information. The control device 150 may analyze a sleep state of the user using his or her different biometric information over time.

For example, the control device 150 may analyze the sleep state of the user using a skin temperature, HRV, and movement information in first time t1. As shown in first region R1 in first time t1, when movement of the user is detected, if a skin temperature is higher than a threshold and if HRV is greater than a threshold, the control device 150 may determine a sleep state of the user as awake state. Particularly, as shown in first region R1, if the skin temperature is higher than the threshold by a desired (or, alternatively, a predetermined) value or more and if the HRV is greater than the threshold by a desired (or, alternatively, a predetermined) value or more, the control device 150 may determine the sleep state of the user as an arousal state in the wake state.

The control device 150 may analyze a sleep state of the user using a skin temperature, HRV, and movement information in second time t2. As shown in second region R2 in second time t2, when movement of the user is not detected, if a skin temperature is lower than the threshold and if HRV is less than the threshold, the control device 150 may determine a sleep state of the user as a NREM sleep state. Particularly, as shown in region R2, if the skin temperature is lower than the threshold by the desired (or, alternatively, the predetermined) value or less and if the HRV is less than the threshold by the desired (or, alternatively, the predetermined) value or less, the control device 150 may determine a sleep state of the user as a deep sleep state in the NREM sleep state.

The control device 150 may analyze a sleep state of the user using movement information and sound information in third time t3. As shown in third region R3 in third time t3, if movement and a sound of the user are greatly detected temporarily at a specific moment, the control device 150 may determine that the user talks in his or her sleep to determine a sleep state of the user as a REM sleep state. In addition, the control device 150 may analyze a sleep state of the user using a skin temperature and HRV information in fourth time t4. As shown in fourth region R4 in fourth time t4, if a skin temperature is temporarily increased and if HRV is greatly increased, the control device 150 may determine a sleep state of the user as a REM sleep state.

The control device 150 may analyze quality of sleep as well as the sleep state of the user using biometric information. As shown in fifth region R5, if a skin impedance value is less than a threshold, the control device 150 may determine sleep quality of the user is bad. As shown in second region R2, if a level of HRV is lower than the threshold, the control device 150 may determine that sleep quality of the user is good. The control device 150 may calculate a value of sleep quality as a numeric value. The value of the sleep quality, included in sleep feedback information, may be provided to the user.

For example, a threshold of biometric information for analyzing a sleep state and sleep quality of the user may be a value preset based on a biological characteristic or an operation characteristic in a sleep state. In other words, the threshold may be determined based on a plurality of biometric information generally detected from users in their sleep states. The determined threshold may be previously stored in the control device 150.

According to an example embodiment of the inventive concepts, the method for analyzing the sleep state of the user at the control device 150 is not limited to an example of FIG. 10. The control device 150 may detect various changes of biometric information measurement values and may analyze a sleep state of the user. As such, the method for analyzing the sleep state of the user according to example embodiments of the inventive concepts may include all methods for analyzing a sleep state from a biometric information measurement value.

Hereinafter, a description will be given in detail of an operation of the control device 150 in operations S140 to S160 of FIG. 4 with reference to FIGS. 11 and 12.

Figure 11:
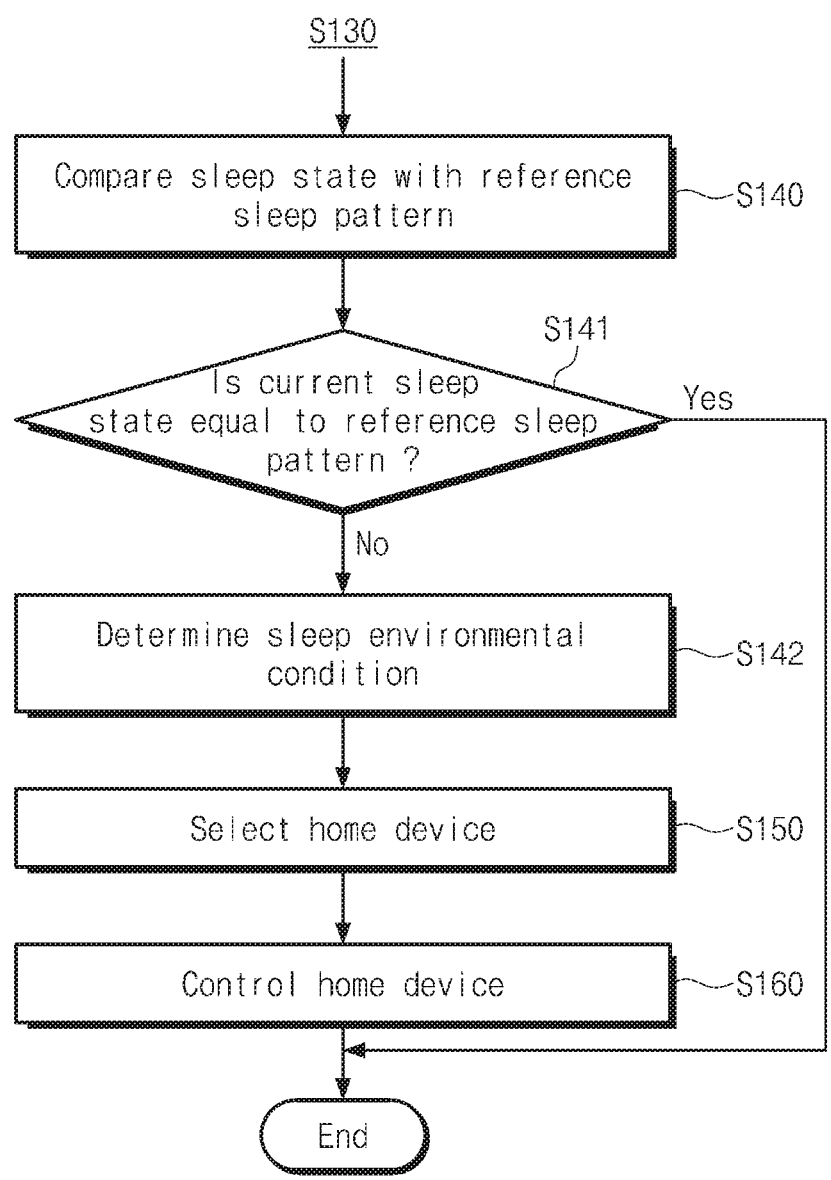
FIG. 11 is a flowchart illustrating a method for controlling a home device according to an example embodiment of the inventive concepts.

FIG. 11 is a flowchart illustrating a method for controlling a home device according to an example embodiment of the inventive concepts. FIG. 12 is a waveform chart illustrating an example of comparing a reference sleep pattern with a current sleep state according to an example embodiment of the inventive concepts.

Figure 12:
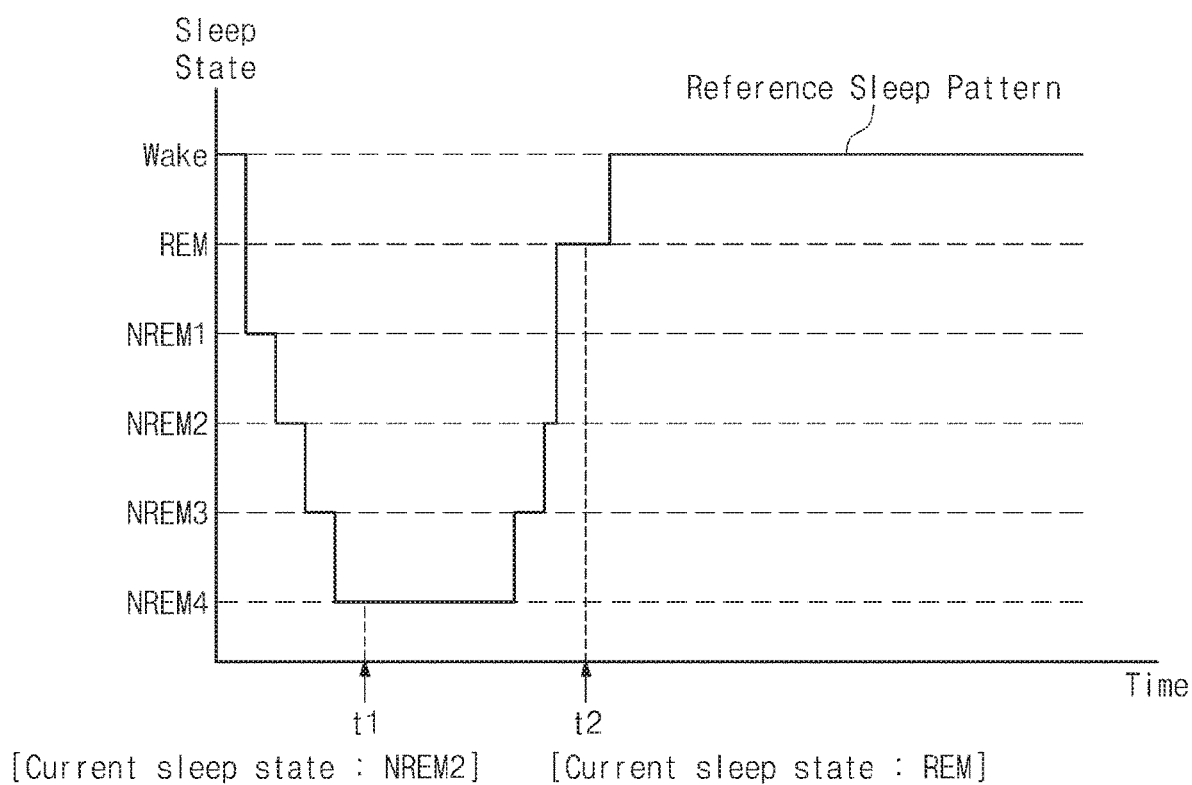
FIG. 12 is a waveform chart illustrating an example of comparing a reference sleep pattern with a current sleep state according to an example embodiment of the inventive concepts.

Referring to FIGS. 2, 11, and 12, in operation S140, a control device 150 may compare a determined reference sleep pattern with a current sleep state of a user. For example, as shown in FIG. 12, first of all, the control device 150 may analyze a current sleep state of the user as a second stage NREM2 of an NREM sleep state in first time t1. A reference sleep pattern determined by the control device 150 may indicate a fourth stage NREM4 of the NREM sleep state in first time t1. The control device 150 may compare the second stage NREM2 of the NREM sleep state which is the current sleep state in first time t1 with the fourth stage NREM4 of the NREM sleep stage of the reference sleep pattern. The control device 150 may analyze a current sleep state of the user as a REM sleep state REM in second time t2. The reference sleep pattern determined by the control device 150 may indicate the REM sleep state in second time t2. The control device 150 may compare the REM sleep state which is the current sleep state in second time t2 with the REM sleep state of the reference sleep pattern.

In operation S141, the control device 150 may determine that the current sleep state is equal to the reference sleep pattern. If the current sleep state of the user is equal to the reference sleep pattern, the control device 150 may not control an operation of a home device 140. For example, as shown in FIG. 12, if both of the reference sleep pattern and the current sleep state of the user are equal to each other as the REM sleep state in second time t2, the control device 150 may not control the home device 140. If the current sleep state of the user is different from the reference sleep pattern, the control device 150 may control an operation of the home device 140. For example, as shown in FIG. 12, if the current sleep state of the user is different from the reference sleep pattern in time t1, the control device 150 may control an operation of the home device 140 for changing a sleep environmental condition.

If the current sleep state of the user is different from the reference sleep pattern, in operation S142, the control device 150 may determine a sleep environmental condition to be changed. The sleep environmental condition may include temperature, light, a sound, a wind, humidity, a height of a pillow, a temperature of the pillow, a shake of a bed, an incline of the bed, or combinations thereof. The sleep environmental condition may include all natural, human elements which have an influence on sleep of the user. The control device 150 may select at least one of a plurality of sleep environment conditions to determine a sleep environmental condition to be changed. For example, the control device 150 may determine temperature and a sound as a sleep environmental condition to be changed.

For example, the control device 150 may determine a sleep environmental condition to be changed, based on biometric information of the user. For example, if a skin temperature of the user is greater than a specific threshold, the control device 150 may determine temperature or a temperature condition of a pillow as a sleep environmental condition to be changed.

The control device 150 may determine a sleep environmental condition to be changed, based on a reference sleep pattern. For example, if the reference sleep pattern indicates a fourth stage of an NREM sleep state NREM4, the control device 150 may determine light and sound conditions as sleep environmental conditions to be changed. The control device 150 may block light and a sound to guide the user to be in a deep sleep state.

If there is a sleep environmental condition which departs from a constant range among a plurality of sleep environmental conditions, the control device 150 may determine the sleep environmental conditions as a sleep environmental condition to be changed. For example, if a sound output from a speaker departs from a desired (or, alternatively, a predetermined) sound level range or if a temperature of a room departs from a desired (or, alternatively, a predetermined) temperature range, the control device 150 may determine a sound and temperature as a sleep environmental condition to be changed.

The control device 150 may determine a desired (or, alternatively, an optimum) sleep environmental condition based on a sleep state change according to the changed sleep environmental condition. For example, the control device 150 may match and store a sleep environmental condition for best moving a sleep state of the user to a sleep state of a reference sleep pattern with a corresponding situation. In a situation where the current sleep state of the user is the second stage of the NREM sleep state NREM2 in first time t1 and where the sleep state of the reference sleep pattern is the fourth stage of the NREM sleep state NREM4 in first time t1, a temperature condition may be determined as a sleep environmental condition for best moving the sleep state of the user to the fourth stage of the NREM sleep state NREM4. In this case, the control device 150 may match and store current sleep state NREM2 of the user and sleep state NREM4 of the reference sleep pattern with a sleep environmental condition (temperature).

The control device 150 may continuously determine whether a sleep environmental condition matched and stored with a specific situation is a desired (or, alternatively, an optimum) condition and may update the stored sleep environmental condition.

In operation S150, the control device 150 may select one or more of the home devices 140 based on the determined sleep environmental condition. For example, if temperature is determined as a sleep environmental condition, the control device 150 may select an air conditioner or a pillow. If light is determined as a sleep environmental condition, the control device 150 may select a lamp or a curtain.

For example, if there are a plurality of home devices 140 for adjusting the same sleep environmental condition, the control device 150 may select the proper home device 140 according to preference of the user. Further, the control device 150 may select the home device 140 in consideration of various elements such as a health condition of the user, a current time, and power usage of the home device 140.

In operation S160, the control device 150 may transmit a control command to the selected ones of the home devices 140 to control an operation of the selected ones of the home devices 140. For example, if a sleep environmental condition arrives at a targeted sleep environmental condition value, the control device 150 may control an operation of the home device 140 to maintain the environmental condition.

The control device 150 may control one or more of the home devices 140 based on sleep time information of the user.

Figure 13:
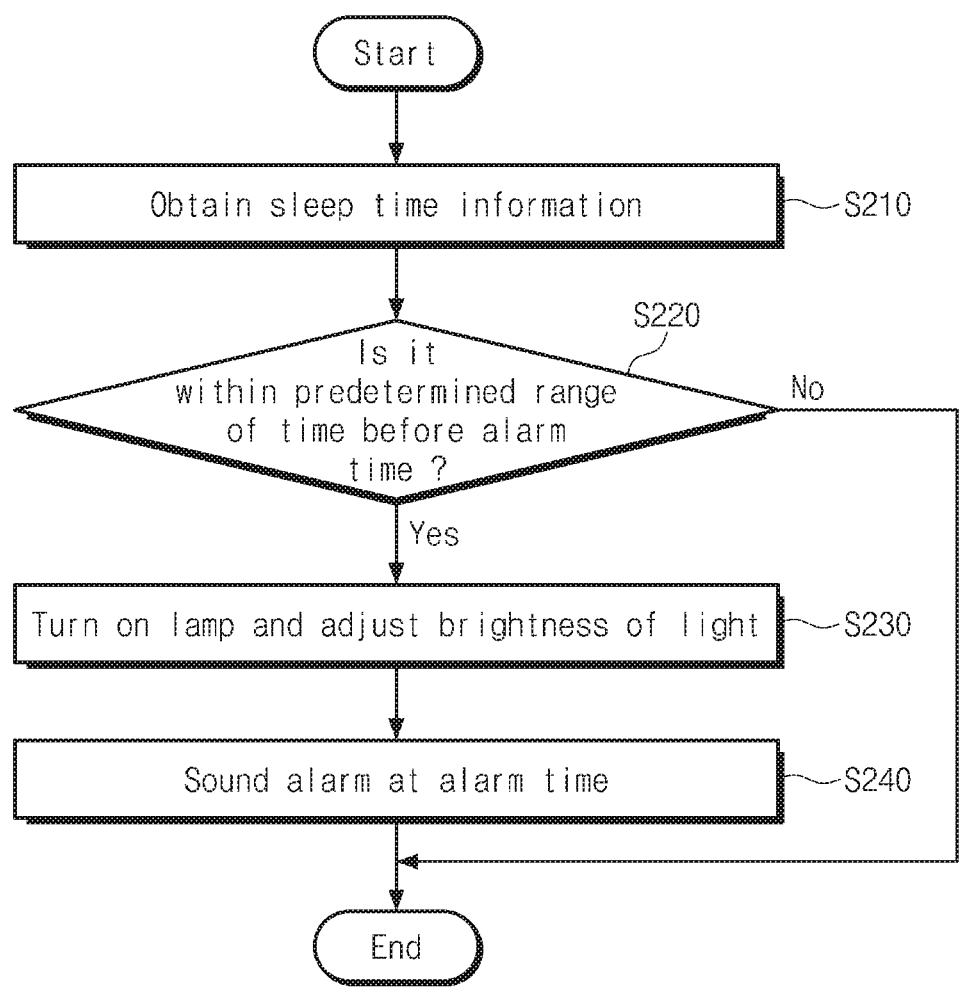
FIG. 13 is a flowchart illustrating an example of controlling a light and a speaker based on sleep time information at a control device according to an example embodiment of the inventive concepts.

FIG. 13 is a flowchart illustrating an example of controlling a lamp and a speaker based on sleep time information at a control device according to an example embodiment of the inventive concepts.

Referring to FIG. 13, the control device 150 may control the home device 140 based on sleep time information.

In operation S210, the control device 150 may obtain sleep time information. The control device 150 may obtain the sleep time information from an alarm time set by the user.

In operations S220 and S230, if a current time is within a desired (or, alternatively, a predetermined) time relative to the alarm time, the control device 150 may turn on a lamp and may adjust brightness of light. The control device 150 may guide a sleep state of the user to a light sleep state through control of the lamp.

In operation S240, if the current time is the alarm time, the control device 150 may output an alarm sound via a speaker. For example, the control device 150 may output an alarm sound via a sensing device 110 which is worn on the user or a separate speaker.

Figure 14:
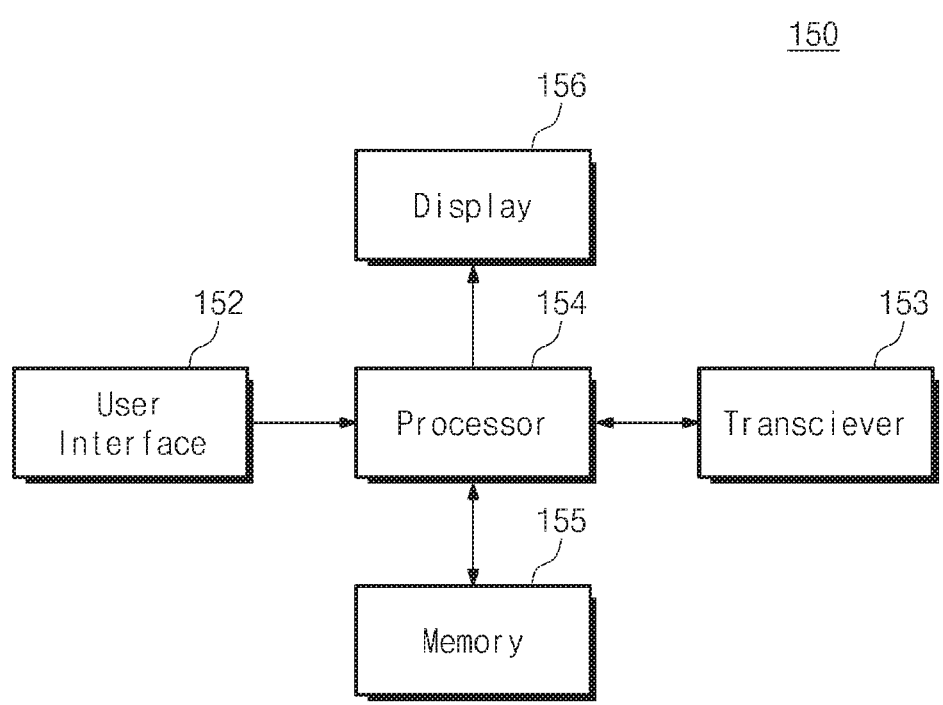
FIG. 14 is a block diagram illustrating a configuration of a control device of FIG. 2.

FIG. 14 is a block diagram illustrating a configuration of a control device of FIG. 2. Referring to FIGS. 2 and 14, a control device 150 may include a user interface 152, a transceiver 153, a processor 154, a memory 155, and a display 156. The control device 150 may be implemented as a device which relays information exchange between a mobile device, such as a smartphone, and a home device 140, such as a home gateway, and an external Internet network.

The user interface 152 may detect a user input and may transmit an input signal corresponding to the user input to the processor 154. The user interface 152 may include a keypad, a touch pad, a jog switch, a dome switch, a microphone, and the like. The control device 150 may obtain sleep related information, such as a value of sleep quality, an alarm time, and information about a preferred home device, via the user interface 152 from a user. The user interface 152 may detect a touch or voice of the user to obtain sleep related information from him or her.

The transceiver 153 may transmit a signal generated by the control device 150 or may receive an external signal. The control device 150 may communicate with a sensing device 110 or an external server (not shown) and a home device 140 via the transceiver 153. The transceiver 153 may exchange data with the outside using communication technology such as wireless local area network (WLAN), wireless-fidelity Zigbee, Bluetooth, Bluetooth low energy (BLE), wireless broadband (Wibro), world interoperability for microwave access (Wimax), or high speed downlink packet access (HSDPA).

For example, the transceiver 153 may receive biometric information of the user, measured by the sensing device 110, or sleep related information of the user, input to the sensing device 110. The transceiver 153 may receive sleep environment information detected by the home device 140 or state information of the home device 140. For example, the transceiver 153 may receive temperature information of a room, detected by an air conditioner, fault information of the air conditioner, or the like.

The transceiver 153 may transmit a control command for changing a sleep environmental condition to the home device 140. The transceiver 153 may transmit a value of sleep quality of the user, analyzed by the control device 150, sleep state information, reference sleep pattern information, operation information about the home device 140, and the like to the sensing device 110 or a user terminal such as a smartphone.

The processor 154 may include a Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

The processor 154 may be configured, through a layout design and/or execution of computer readable instructions stored in the memory 155, as a special purpose computer to analyze a current sleep state of a user based on biometric information associated with the user, and selectively control one or more of the home devices based on the current sleep state of the user. Therefore, the processor 154 may improve the functioning of the control device 130, 150 of an IoT system itself by allowing the control device 130, 150 to improve sleep quality of the user by adjusting a sleep environment based on real time characteristics and environment of the particular user.

The processor 154 may control each element of the control device 150. The processor 154 may generate a control command for an operation of the home device 140. For example, the processor 154 may receive sleep related information, such as a value of sleep quality, an alarm time, and information about a preferred home device, from the user interface 152 and may generate a control command for changing a sleep environmental condition. The processor 154 may generate a control command for changing a sleep environmental condition using biometric information of the user, received via the transceiver 153. The processor 154 may transmit the control command to the home device 140 via the transceiver 153.

The processor 154 may generate a sleep pattern based on information collected via the user interface 152 and the transceiver 153 and may analyze a sleep state of the user. The processor 154 may store sleep patterns generated in various situations and sleep state information in the memory 155. The processor 154 may generate a plurality of sleep patterns corresponding to respective situations suitable for the user through machine learning. The processor 154 may determine a reference sleep pattern suitable for a situation of the user among a plurality of stored sleep patterns. For example, as shown in FIG. 8, the processor 154 may determine a reference sleep pattern in consideration of sleep time information, basic information of the user, and the like. The processor 154 may compare the determined reference sleep pattern with analyzed sleep state information of the user to determine whether to control the home device 140.

If the reference sleep pattern is different from a current sleep state of the user, the processor 154 may determine a sleep environmental condition to be changed. For example, the processor 154 may determine a desired (or, alternatively, an optimum) sleep environmental condition for moving a current sleep state of the user to a sleep state of the reference sleep pattern through machine learning. The processor 154 may select the home device 140 which may change the determined sleep environmental condition. The processor 154 may select the home device 140 in consideration of various elements, such as a health condition of the user, a current time, and power usage, among the plurality of home devices 140 which may change the determined sleep environmental condition.

The processor 154 may generate a value of sleep quality from biometric information of the user, received from the transceiver 153. For example, the processor 154 may calculate a stress level during sleep of the user using information such as HRV or GSR. The processor 154 may transmit a value for sleep quality, such as the calculated stress level, as sleep feedback information to the sensing device 110 or a user terminal. Further, the processor 154 may output sleep feedback information including a value of sleep quality on the display 156.

The memory 155 may store data which is received or generated by the control device 150. The memory 155 may store sleep related information and biometric information, received from the user interface 152 or the transceiver 153. The memory 155 may store a sleep pattern generated by the processor 154 and sleep state information of the user. The memory 155 may store a reference sleep pattern determined by the processor 154. The memory 155 may match a desired (or, alternatively, an) optimum sleep pattern for a specific situation with a condition of the situation and may store the matched information in the form of metadata. For example, as shown in FIG. 8, the memory 155 may store sleep pattern information matched with a condition such as a sleep time and basic information of the user.

The memory 155 may store sleep environmental condition information according to a reference sleep pattern and a sleep state of the user in the form of metadata. For example, if a reference sleep pattern is a fourth stage NREM4 of an NREM sleep state and if a sleep state of the user is a REM sleep state, the memory 155 may match and store information about a desired (or, alternatively, an optimum) environmental condition to change the sleep state of the user to the fourth stage of the NREM sleep state NREM4 with the state information.

The memory 155 may be implemented as at least one type of a storage medium among a flash memory, a hard disc, a secure digital (SD) card memory, an extreme digital (XD) card memory, a random access memory (RAM), a static RAM (SRAM), a read-only memory (ROM), an electrically erasable programmable ROM (EEPROM), a programmable ROM (PROM), a magnetic memory, a magnetic disc, and an optical disc.

The display 156 may display information processed by the control device 150. The display 156 may display a value of sleep quality of the user, operation information about the home device 140, a reference sleep pattern, sleep state information, and the like. The user may verify items managed for a deep sleep from information displayed on the display 156.

The control device 150 of FIG. 14 may obtain biometric information of the user, detected from the separate sensing device 110 through the transceiver 153. However, the control device according to example embodiments of the inventive concepts are not limited thereto. The control device according to example embodiments of the inventive concepts may further include a sensor (not shown) for sensing biometric information of the user. The sensor may transmit biometric information of the user to the processor 154. The control device including the sensor may be a wearable device worn or attached to a body of the user.

Figure 15:
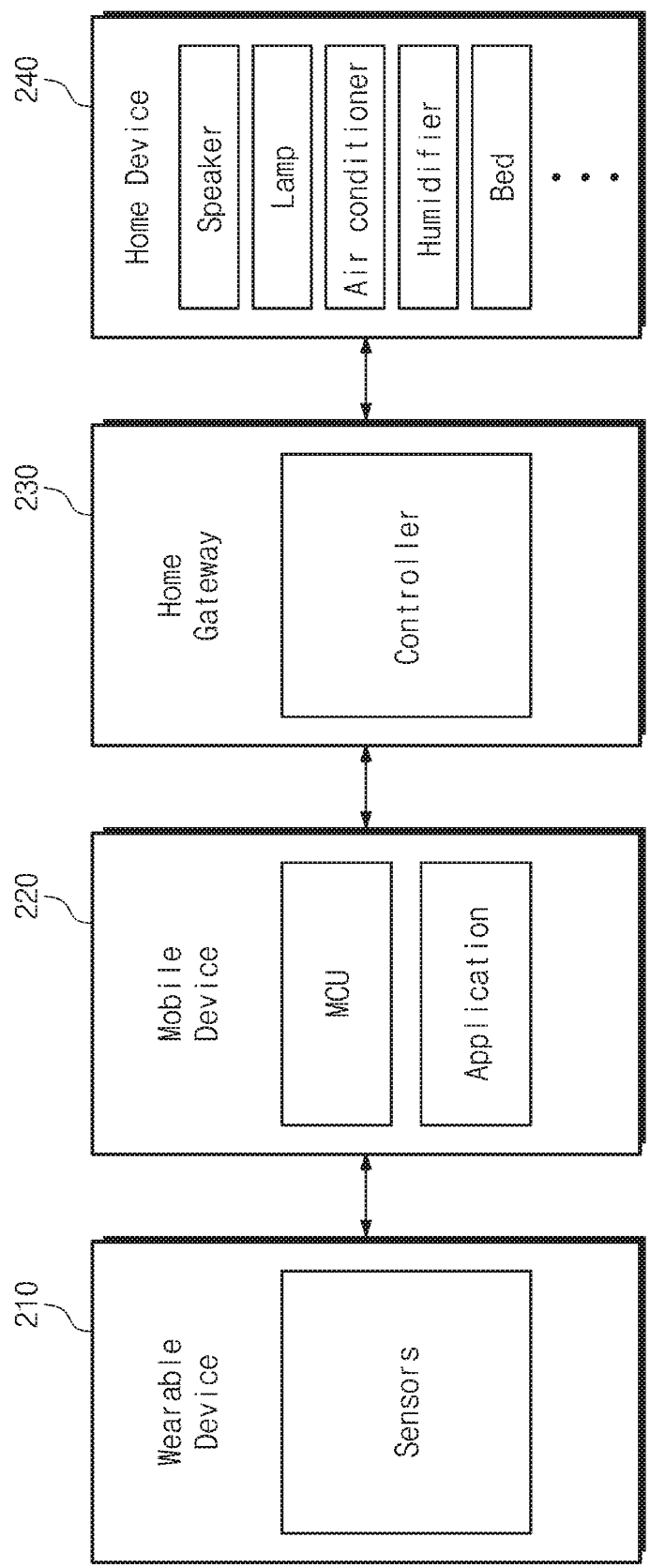
FIG. 15 is a block diagram illustrating an example of a home device control system according to an example embodiment of the inventive concepts.

FIG. 15 is a block diagram illustrating an example of a home device control system according to an example embodiment of the inventive concepts.

Referring to FIGS. 14 and 15, the home device control system may include a wearable device 210, a mobile device 220, a home gateway 230, and a home device 240. The wearable device 210 may detect biometric information of the user from sensors worn or attached to his or her body. For example, the wearable device 210 may be a smart band or a smart watch.

The mobile device 220 may include a function of a control device 150. The mobile device 220 may perform a function of the control device 150 through a micro controller unit (MCU). The MCU may include an application processor (AP), a memory, a communication module, and the like of a smartphone and may be configured as one chip. A control signal for the home device 240, generated by the MCU, may be transmitted to the home gateway 230. The home gateway 230 may control an operation of the home device 240 based on the control signal received from the mobile device 220.

The mobile device 220 may include an application for providing the convenience of managing a sleep environment of the user. The mobile device 220 may receive sleep related information, such as a value of sleep quality, an alarm time, basic information of a user, and information about a preferred home device, through the application from the user. The mobile device 220 may provide a value of sleep quality, operation information of the home device 240, a reference sleep pattern, sleep state information, and the like, analyzed by the mobile device 220, to the user through the application.

The home gateway 230 may receive a control command for the home device 240 from the mobile device 220 and may control the home device 240. The home gateway 230 may receive a control command and may convert the received control command to a signal finally recognizable by the home device 240, thus transmitting the converted signal to the home device 240. The home gate way 230 may play a relay role between the mobile device 220 and the home device 240, and a control of the home gateway 230 may process data necessary for a relay process.

The home device 240 may receive a control command from the home gateway 230 and may process and execute the received command. The home device 240 may include a speaker, a lamp, an air conditioner, a humidifier, a bed, a curtain, and the like. The home device 240 may adjust a sleep environment, such as a sound, light, temperature, humidity, and a wind, for having an influence on sleep of the user. The home device 240 may detect a sleep environmental element and may transmit information about a sleep environment to the home gateway 230.

The apparatus and method for controlling the home device may enhance sleep quality of the user by adjusting his or her sleep environment using the sensing device 110 which may be easily worn on the user. Further, according to example embodiments of the inventive concepts, the apparatus and method for controlling the home device may provide a desired (or, alternatively, an optimum) sleep environment to the user by generating sleep patterns suitable for various situations of the user.

According to example embodiments of the inventive concepts, the home device control device and the operation method thereof may enhance sleep quality of the user. Thus, the home device control device and the operation method thereof may provide a desired (or, alternatively, an optimum) sleep environment to the user.

While example embodiments of the inventive concepts have been described with reference to some example embodiments, it will be apparent to those skilled in the art that various changes and modifications may be made without departing from the spirit and scope of the inventive concepts. Therefore, it should be understood that the above example embodiments are not limiting, but illustrative.

What is claimed is:

1. A method of operating a control device for controlling a home device, the control device including a memory and a processor, the method comprising:
  determining a reference sleep pattern among a plurality of sleep patterns based on one or more of sleep time information associated with a user and basic information associated with the user;
  analyzing a current sleep state of the user based on biometric information of the user, the biometric information sensed from a wearable device of the user and including at least one of (i) a skin temperature detected from the user, (ii) heart rate variability (HRV) of the user, (iii) movement of the user, (iv) a sound generated by the user, and (v) skin impedance of the user;
  comparing a reference sleep state of the reference sleep pattern with the current sleep state;
  determining variations to make to a sleep environmental condition to guide the current sleep state of the user to be in the reference sleep state when the reference sleep state is a deeper sleep state than the current sleep state, the variations in the sleep environmental condition including variations to one or more of a room temperature, a light, a humidity, a wind, a height of a pillow, a temperature of the pillow, an incline of a bed, and a shake of the bed;
  controlling the home device to make the variations to the sleep environmental condition such that the current sleep state approaches the reference sleep state; and
  transmitting sleep feedback information to the wearable device of the user, after sleep of the user is completed, the sleep feedback information including information on sleep quality, a sleep state, and the reference sleep pattern of the user during a sleep time, and operation information of the home device.

2. The method of claim 1, further comprising:
collecting the sleep time information based on an alarm time of the user, wherein
the basic information includes one or more of a gender, an age, a health condition, and a body characteristic of the user.

3. The method of claim 1, wherein
the determining the sleep environmental condition includes collecting an alarm time of the user from the user, and
the controlling the home device includes,
controlling a lamp of the home device when a current time is within a set range of time from the alarm time; and
controlling a speaker of the home device at the alarm time.

4. The method of claim 1, wherein each of the plurality of sleep patterns includes sleep state information changed over time, and wherein
the comparing includes determining whether the current sleep state is equal to the reference sleep state of the reference sleep pattern.

5. A control device, comprising:
a memory configured to store a plurality of sleep patterns; and
a processor configured to,
determine a reference sleep pattern among the plurality of sleep patterns based on one or more of sleep time information associated with a user and basic information associated with the user,
analyze a current sleep state of the user based on biometric information of the user, the biometric information sensed from a wearable device of the user and including at least one of (i) a skin temperature detected from the user, (ii) heart rate variability (HRV) of the user, (iii) movement of the user, (iv) a sound generated by the user, and (v) skin impedance of the user,
compare a reference sleep state of the reference sleep pattern with the current sleep state,
determine variations to make to a sleep environmental condition to guide the current sleep state of the user to be in the reference sleep state when the reference sleep state is a deeper sleep state than the current sleep state of the user, the variations in the sleep environmental condition including variations to one or more of a room temperature, a light, a humidity, a wind, a height of a pillow, a temperature of the pillow, an incline of a bed, and a shake of the bed,
control a home device to make the variations to the sleep environmental condition such that the current sleep state approaches the reference sleep state, and
transmit sleep feedback information to the wearable device of the user, after sleep of the user is completed, the sleep feedback information including information on sleep quality, a sleep state, and the reference sleep pattern of the user during a sleep time, and operation information of the home device.

6. The control device of claim 5, wherein the processor is configured to collect the sleep time information based on an alarm time of the user, and wherein
the basic information includes one or more of a gender, an age, a health condition, and a body characteristic of the user.

7. The control device of claim 5, wherein each of the plurality of sleep patterns includes sleep state information changed over time, and wherein
the processor is configured to compare the reference sleep pattern with the current sleep state of the user by determining whether the current sleep state is equal to the reference sleep state of the reference sleep pattern.

8. The control device of claim 5, further comprising:
a transceiver configured to receive the biometric information from an external sensing device, and to transmit the biometric information to the processor.

9. A control device configured to control a home device, the control device comprising:
a sensor configured to sense biometric information of a user, the biometric information including at least one of (i) a skin temperature detected from the user, (ii) heart rate variability (HRV) of the user, (iii) movement of the user, (iv) a sound generated by the user, and (v) skin impedance of the user;
a memory configured to store a plurality of sleep patterns; and
a processor configured to,
determine a reference sleep pattern among the plurality of sleep patterns based on one or more of sleep time information associated with the user and basic information associated with the user,
analyze a current sleep state of the user based on the biometric information of the user,
compare a reference sleep state of the reference sleep pattern with the current sleep state,
determine variations to make to a sleep environmental condition to guide the current sleep state of the user to be in the reference sleep state when the reference sleep state is a deeper sleep state than the current sleep state of the user, the variations in the sleep environmental condition including variations to one or more of a room temperature, a light, a humidity, a wind, a height of a pillow, a temperature of the pillow, an incline of a bed, and a shake of the bed,
control the home device to make the variations to the sleep environmental condition such that the current sleep state approaches the reference sleep state, and
transmit sleep feedback information to a wearable device of the user, after sleep of the user is completed, the sleep feedback information including information on sleep quality, a sleep state, and the reference sleep pattern of the user during a sleep time, and operation information of the home device.

10. The control device of claim 9, wherein the processor is configured to collect the sleep time information based on an alarm time of the user, and wherein
the basic information includes one or more of a gender, an age, a health condition, and a body characteristic of the user.

11. The control device of claim 9, wherein each of the plurality of sleep patterns includes sleep state information changed over time, and wherein
the processor is configured to compare the reference sleep pattern with the current sleep state of the user by determining whether the current sleep state is equal to the reference sleep state of the reference sleep pattern.

* * * * *